US012201607B2

(12) United States Patent
 Criscione

(10) Patent No.: US 12,201,607 B2
(45) Date of Patent: *Jan. 21, 2025

(54) COMPOSITIONS AND METHODS FOR PREVENTING AND TREATING CONDITIONS

(71) Applicant: Ansella Therapeutics, Inc., Lowell, MA (US)

(72) Inventor: Jason M. Criscione, Chelmsford, MA (US)

(73) Assignee: Ansella Therapeutics, Inc., Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/867,045

(22) Filed: May 5, 2020

(65) Prior Publication Data

US 2020/0360340 A1    Nov. 19, 2020

Related U.S. Application Data

(63) Continuation of application No. 16/220,517, filed on Dec. 14, 2018, now Pat. No. 10,668,046.

(60) Provisional application No. 62/609,127, filed on Dec. 21, 2017, provisional application No. 62/607,286, filed on Dec. 18, 2017.

(51) Int. Cl.
| | |
|---|---|
| A61K 31/355 | (2006.01) |
| A61K 9/00 | (2006.01) |
| A61K 9/06 | (2006.01) |
| A61K 9/107 | (2006.01) |
| A61K 31/41 | (2006.01) |
| A61K 45/06 | (2006.01) |
| A61P 17/02 | (2006.01) |
| A61P 27/02 | (2006.01) |
| A61P 39/06 | (2006.01) |

(52) U.S. Cl.
CPC .......... *A61K 31/355* (2013.01); *A61K 9/0014* (2013.01); *A61K 9/0034* (2013.01); *A61K 9/06* (2013.01); *A61K 9/107* (2013.01); *A61K 31/41* (2013.01); *A61P 17/02* (2018.01); *A61P 27/02* (2018.01); *A61P 39/06* (2018.01); *A61K 45/06* (2013.01)

(58) Field of Classification Search
CPC .......... A61K 9/107; A61K 8/064; A61K 9/06; A61K 9/0034; A61K 9/0014
See application file for complete search history.

(56) References Cited

U.S. PATENT DOCUMENTS

| | | |
|---|---|---|
| 3,489,690 A | 1/1970 | Lachampt et al. |
| 4,847,071 A | 7/1989 | Bissett et al. |
| 5,256,422 A | 10/1993 | Albert et al. |
| 5,942,213 A | 8/1999 | Bara et al. |
| 6,121,373 A | 9/2000 | Starch |
| 6,537,537 B2 | 3/2003 | Deckner et al. |
| 6,570,054 B1 | 5/2003 | Gatto et al. |
| 8,048,952 B2 | 11/2011 | Wynne et al. |
| 10,668,046 B2 | 6/2020 | Criscione |
| 2002/0022040 A1 | 2/2002 | Robinson et al. |
| 2005/0048019 A1 | 3/2005 | Kropke et al. |
| 2005/0112078 A1 | 5/2005 | Boddupalli et al. |
| 2006/0003033 A1 | 1/2006 | McClellan et al. |
| 2006/0051383 A1 | 3/2006 | Emig et al. |
| 2006/0104940 A1 | 5/2006 | Heinrichs et al. |
| 2009/0035236 A1 | 2/2009 | Maes et al. |
| 2011/0086807 A1 | 4/2011 | Soo |
| 2011/0195103 A1 | 8/2011 | Perez et al. |
| 2019/0183854 A1 | 6/2019 | Criscione |

FOREIGN PATENT DOCUMENTS

| | | |
|---|---|---|
| EP | 0330369 A1 | 8/1989 |
| EP | 0846461 A1 | 6/1998 |
| JP | H06506487 A | 7/1994 |
| JP | H07506529 A | 7/1995 |
| JP | 2003104826 A | 4/2003 |
| JP | 2003528821 A | 9/2003 |
| JP | 2004502716 A | 1/2004 |
| JP | 2004506613 A | 3/2004 |
| JP | 2005206573 A | 8/2005 |
| JP | 2007534661 A | 11/2007 |
| JP | 2008539176 A | 11/2008 |
| JP | 2009524609 A | 7/2009 |
| JP | 5474768 B2 | 2/2014 |
| WO | 9319723 A1 | 10/1993 |
| WO | 9321930 A1 | 11/1993 |
| WO | 9826752 A1 | 6/1998 |
| WO | 2006110271 A1 | 10/2006 |
| WO | 2010079054 A1 | 7/2010 |
| WO | 2012089474 A1 | 7/2012 |
| WO | 2014161863 A1 | 10/2014 |

OTHER PUBLICATIONS

Chen et al., Journal of Medicinal Chemistry, 2001, American Chemical Society, vol. 44, pp. 2374-2377.*
Dykhuizen, Antonie van Leeuwenhoek, 1998, Kluwer Academic Publishers, vol. 73, pp. 25-33.*
Foroumadi et al., European Journal of Medicinal Chemistry, 2003, Elsevier, vol. 38, pp. 851-854.*
Huczynski et al., Journal of Molecular Structure, 2008, Elsevier, vol. 891, pp. 481-490.*
Bornstein et al. (2008) "Involvement of heparanase in the pathogenesis of localized vulvodynia," International Journal of Gynecological Pathology. 27(1):136-141.
Burrows et al. (2012) "The effects of hormonal contraceptives on female sexuality: a review," The journal of sexual medicine. 9(9):2213-2223.

(Continued)

*Primary Examiner* — Shobha Kantamneni
(74) *Attorney, Agent, or Firm* — Mintz Levin Cohn Ferris Glovsky and Popeo, P.C.

(57) ABSTRACT

Provided herein are compositions comprising a stable water-in-silicone emulsion, and methods and kits comprising the compositions for treating conditions.

10 Claims, 15 Drawing Sheets

(56) References Cited

OTHER PUBLICATIONS

Gambichler et al. (2012) "Differential expression of connective tissue growth factor and extracellular matrix proteins in lichen sclerosus," Journal of the European Academy of Dermatology and Venereology. 26(2):207-212.
Goldstein et al. (2010) "Can oral contraceptives cause vestibulodynia?" The journal of sexual medicine. 7(4):1585-1587.
Iriyama et al. (2010) "Heparanase activation induces epidermal hyperplasia, angiogenesis, lymphangiogenesis and wrinkles," Experimental dermatology. 19(11):965-972.
Kahan et al. (2009) "Stress, immunity and skin collagen integrity: evidence from animal models and clinical conditions," Brain, behavior, and immunity. 23(8)1089-1095.
Kurdykowski et al. (2012) "Ultraviolet-B irradiation induces epidermal up-regulation of heparanase expression and activity," Journal of Photochemistry and Photobiology B: Biology. 106:107-112.
Morita et al. (2009) "Molecular basis of tobacco smoke-induced premature skin aging," Journal of Investigative Dermatology Symposium Proceedings. 14(1):53-55.
Oikarinen et al. (1991) "New aspects of the mechanism of corticosteroid-induced dermal atrophy," Clinical and experimental dermatology. 16(6):416-419.
Wysocki et al. (2014) "Management of vaginal atrophy: implications from the REVIVE survey," Clinical Medicine Insights: Reproductive Health. 8:23-30.
International Search Report with Written Opinion corresponding to International Patent Application No. PCT/US18/65710, dated Feb. 22, 2019, 14 pages.
Kellogg-Spadt (2010) "Vulvovaginal Atrophy," Advance for nurse practitioners. 18(4):31-55.
Dahms et al. (1995) "New formulation possibilities offered by silicone copolyols," Cosmetics and Toiletries-Carol Stream. 110(3):91-101.
Delvalle et al. (2014) "New Formulation Possibilities with a Water-in-oil Silicone Emulsifier Suitable for PEG-free Systems," Dow Corning Co. Ltd. 1:1-20.
Fengyan et al. (2011) "Factors Influencing Droplet Size of Silicone Oil Emulsion with High Solid Content," China Petroleum Processing and Petrochemical Technology. 13(3):21-26.
Hamelau et al. (2015) "Spotlight Emulsion Technology for Topical Pharmaceutical and Medical Device," Dow Corning Co. Ltd. 5:1-4.
Nam et al. (2010) "Silicone oil emulsions stabilized by semi-solid nanostructures entrapped at the interface," Journal of Colloid and Interface Science. 351(1):102-107.
Nazir et al. (2014) "Silicone oil emulsions: strategies to improve their stability and applications in hair care products," International Journal of Cosmetic Science. 36(2):124-133.
O'Lenick (May 2000) "Silicone Emulsions and Surfactants-A Review," Silicone Spectator. 1:1-18.
Patel et al. (Sep. 2015) "Silicone Oil Emulsification in Retina Surgery," Retina Today. 1:29-32.
Prospector (2018) "Sunscreen: Water in Silicone + Oil Emulsion (Formulation #02207)," Dow Chemical—Home and Personal Care. 1:1-2. [Abstract].
Sainath et al. (2014) "Electrical Properties of Silicone Oil-Water Interface in the Presence of Ionic Surfactants and Salt: Importance in the Stability of Oil-in-Water Emulsions," Chemical Engineering Communications. 201(12):1645-1663.
Sakai et al. (2013) "Water-in-oil emulsions prepared by peptide-silicone hybrid polymers as active interfacial modifier: Effects of silicone oil species on dispersion stability of emulsions," Journal of Oleo Science. 62(7):505-511.
Shin-Etsu (Feb. 2017) "Silicone Emulsions," Shin-Etsu Chemical Co., Ltd. 1:1-10.
Somasundaran et al. (2006) "Silicone emulsions," Advances in Colloid and Interface Science. 128: 103-109.
Van Reeth et al. (2003) "New Formulating Options with Silicone Emulsifiers," Dow Corning Co. Ltd. 1:1-7.
Zelisko et al. (2008) "Water-in-silicone oil emulsion stabilizing surfactants formed from native albumin and ?, ?—triethoxysilylpropyl-polydimethylsiloxane," Biomacromolecules. 9(8):2153-2161.
Campana-Seoane et al. (2014) "Bioadhesive Emulsions for Control Release of Progesterone Resistant to Vaginal Fluids Clearance", International Journal of Pharmaceutics, 477(1-2):495-505.
Chaomei et al. (Aug. 2014) "Chinese Medicine Pharmacy", Chinese Pharmaceutical Science and Technology Press, p. 140.
Ming et al. (Jul. 2016) "Chinese Medicine Pharmacy", Chinese Medicine Press, p. 148.

\* cited by examiner

Day 6

Day 1

Day 1

Day 31

Day 1

Day 1

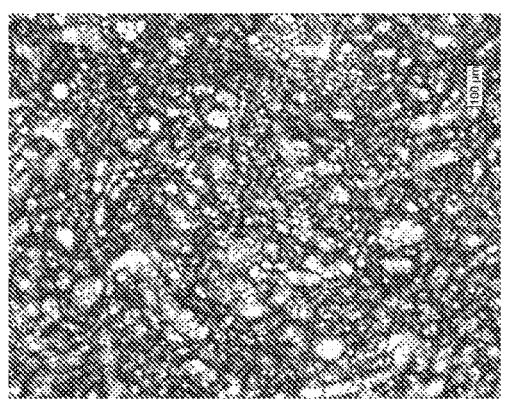
FIG. 5C  Day 14
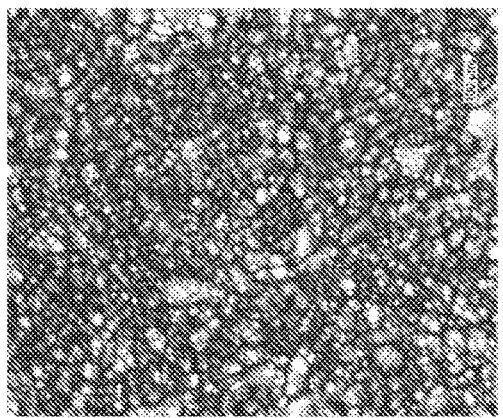
FIG. 5B  Day 1
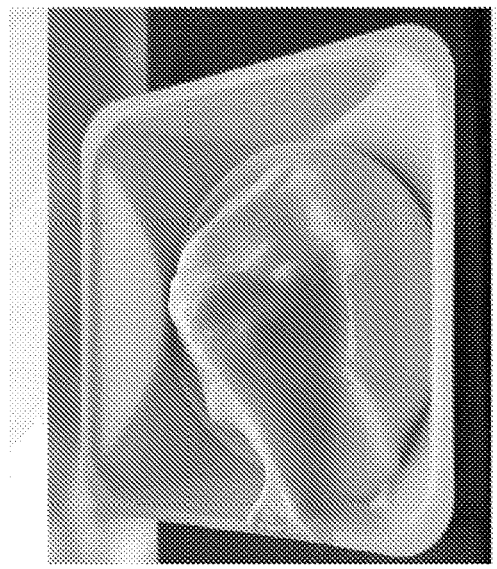
FIG. 5A  Day 1

COMPOSITIONS AND METHODS FOR PREVENTING AND TREATING CONDITIONS

RELATED APPLICATIONS

This application is a continuation of U.S. application Ser. No. 16/220,517, filed Dec. 14, 2018, which claims benefit of priority to U.S. Provisional Application No. 62/609,127, filed Dec. 21, 2017, and U.S. Provisional Application No. 62/607,286, filed Dec. 18, 2017, the entire contents of each of which are incorporated herein by reference.

FIELD OF THE INVENTION

The present invention relates to compositions, methods, and kits for vulvovaginal application and other conditions in a subject.

BACKGROUND

Various compositions are needed to provide lubricity and/or to protect skin and other tissue from damage and/or infection. Such compositions are useful alone or with one or more active and/or bioactive agents, wherein the composition serves as a drug delivery vehicle (e.g., as a transdermal drug delivery vehicle).

In addition, vulvovaginal health continues to be an overlooked medical need, as most markets in this area are largely undifferentiated, especially with respect to over-the-counter or non-prescription products. For this reason, gynecological patients across all demographics, from pre-menopause to post-menopause, who are suffering from one or more vulvovaginal conditions are often treated with prescription products or regimens that typically have undesired product characteristics including, (1) insufficient efficacy duration from a single application, (2) inadequate restoration of physiological stasis, (3) undesired side effects, and (4) untenable health risks.

Thus, there remains a need for a variety of compositions that provide lubricity, protect skin and other tissue, and/or facilitate drug delivery. In particular, there is a need for compositions and formulations capable of providing vulvovaginal symptom relief, treating underlying pathophysiology or infection of the vulvovaginal anatomy, or prophylactically protecting the vulvovaginal anatomy, with respect to a number of vulvovaginal health conditions.

SUMMARY

Provided herein are, inter alia, compositions, formulations and methods that provide lubricity, protect skin, mucosa, and other tissues, and facilitate drug delivery. Compositions, formulations and methods are also provided for treating, preventing, and/or reducing the symptoms of severity of vulvovaginal and other conditions. Provided herein are vulvovaginal compositions designed to provide vulvovaginal symptom relief, treat underlying pathophysiology or infection of the vulvovaginal anatomy, or prophylactically protect the vulvovaginal anatomy in a subject. In some embodiments, the vulvovaginal compositions comprise a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent. In other embodiments, the vulvovaginal compositions consist of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent. In other embodiments, the vulvovaginal compositions consist essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent.

Compositions, formulations and methods are also provided for treating or protecting the skin. Provided herein are dermatological compositions designed to provide treat or protect the skin in a subject. In some embodiments, the dermatological compositions comprise a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, a ceramide, and an active agent. In other embodiments, the dermatological compositions consist of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, a ceramide, and an active agent. In other embodiments, the dermatological compositions consist essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, a ceramide and an active agent.

Also provided herein are methods for preventing or treating a vaginal condition in a subject, the method comprising administering to a subject a composition comprising a stable water-in-silicone emulsion, wherein the emulsion has a sterol at a concentration from about 0.1% to about 4% by weight of the total weight of the emulsion. In embodiments, the composition is administered into the vagina, onto and/or around the vulva, or any combination thereof.

In other examples, the methods described herein are used for preventing or treating a vaginal condition, including menopause, peri-menopause, post-menopause, vaginal dryness, dyspareunia, a bacterial infection, a viral infection, or a fungal infection.

In embodiments, the methods described herein provide a therapeutically effective dose for up to 1 hour, 2 hours, 3 hours, 6 hours, 9 hours, 12 hours, 18 hours, 24 hours, 48 hours, 3 days, 5 days, 7 days, or 14 days. Furthermore, the methods comprise administering the composition every 1 hour, 2 hours, 3 hours, 6 hours, 9 hours, 12 hours, 18 hours, 24 hours, 48 hours, 3 days, 5 days, 7 days, or 14 days.

Also provided herein are methods of preparing a water-in-silicone emulsion comprising preparing an aqueous phase comprising water, a pH buffering system, at least one active or bioactive agent, and a preservative, and separately preparing a silicone phase comprising a silicone oil, a silicone gum, and a sterol, a fatty acid, a tocopherol and a preservative, and adding the aqueous phase to the silicone phase, and mixing the combined phases until the water-in-silicone emulsion is formed, wherein the silicone phase comprises about 20-80% by weight of the composition, and the aqueous phase comprises about 20-80% by weight of the composition, based on the total weight of the composition. In embodiments, the method further includes adding the aqueous phase to the silicone phase under high shear mixing, e.g., where the high shear mixing utilizes a rotor-stator homogenizer.

Methods to provide vulvovaginal symptom relief, treat underlying pathophysiology or infection of the vulvovaginal anatomy, or prophylactically protect the vulvovaginal anatomy in a subject comprising administering to said subject a vulvovaginal composition comprising, consisting of, or consisting essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent, are also disclosed herein.

Methods to treat and protect the skin in a subject comprising administering to said subject a dermatological composition comprising, consisting of, or consisting essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, a ceramide, and an active agent, are also disclosed herein.

Further provided are kits for producing vulvovaginal compositions to provide vulvovaginal symptom relief, treat underlying pathophysiology or infection of the vulvovaginal anatomy, or prophylactically protect the vulvovaginal anatomy in a subject.

Further provided are kits for producing dermatological compositions to treat and protect the skin in a subject.

BRIEF DESCRIPTION OF THE DRAWINGS

This invention will be more fully understood from the following detailed description taken in conjunction with the accompanying drawings, in which:

FIG. 1A shows an exemplary physicochemical orientation of the emulsifier, cell membrane fluidity enhancing agent, and fatty acid constituents, wherein only the emulsifier stabilizes the water and silicone interface. FIG. 1B shows a second exemplary physicochemical orientation of the emulsifier, cell membrane fluidity enhancing agent, and fatty acid constituents, wherein the emulsifier, cell membrane fluidity enhancing agent, and fatty acid cooperatively stabilize the water and silicone interface.

FIG. 2A shows an exemplary physicochemical orientation of the emulsifier, cell membrane fluidity enhancing agent, and fatty acid constituents, wherein only the emulsifier stabilizes the water and silicone interface. FIG. 2B shows a second exemplary physicochemical orientation of the emulsifier, cell membrane fluidity enhancing agent, and fatty acid constituents, wherein the emulsifier, cell membrane fluidity enhancing agent, and fatty acid cooperatively stabilize the water and silicone interface.

FIG. 3A is a macroscopic optical image of Formulation #8 on day 1. FIG. 3B is an optical microscopic image of Formulation #8 on day 1. FIG. 3C is an optical microscopic image of Formulation #8 on day 6. Scale bar is 300 microns.

FIG. 4A is a macroscopic optical image of Formulation #9 on day 1. FIG. 4B is an optical microscopic image of Formulation #9 on day 1. FIG. 4C is an optical microscopic image of Formulation #9 on day 31. Scale bar is 100 microns.

FIG. 5A-5C illustrates optical imaging of Formulation #10. FIG. 5A is a macroscopic optical image of Formulation #10 on day 1. FIG. 5B is an optical microscopic image of Formulation #10 on day 1. FIG. 5C is an optical microscopic image of Formulation #10 on day 14. Scale bar is 100 microns.

FIG. 6A is a macroscopic optical image of Formulation #13 on day 1. FIG. 6B is an optical microscopic image of Formulation #13 on day 1. FIG. 6C is a macroscopic optical image of Formulation #14 on day 1. FIG. 6D is an optical microscopic image of Formulation #14 on day 1. FIG. 6E is an optical image of Formulation #14 showing phase separation. Scale bar is 100 microns.

FIG. 7A is a flow stress sweep of Formulation #9 at 25° C., wherein viscosity is plotted against shear rate. FIG. 7B is a flow stress sweep of Formulation #9 at 25° C., wherein viscosity is plotted against stress. FIG. 7C is a flow stress sweep of Formulation #9 at 37° C., wherein viscosity is plotted against shear rate. FIG. 7D is a flow stress sweep of Formulation #9 at 37° C., wherein viscosity is plotted against stress.

FIG. 8A is an oscillatory amplitude sweep of Formulation #9 at 25° C. FIG. 8B is an oscillatory amplitude sweep of Formulation #9 at 37° C.

FIG. 9A is an oscillatory frequency sweep of Formulation #9 at 25° C. FIG. 9B is an oscillatory frequency sweep of Formulation #9 at 37° C.

DETAILED DESCRIPTION OF ILLUSTRATIVE EMBODIMENTS

Figure 1A:
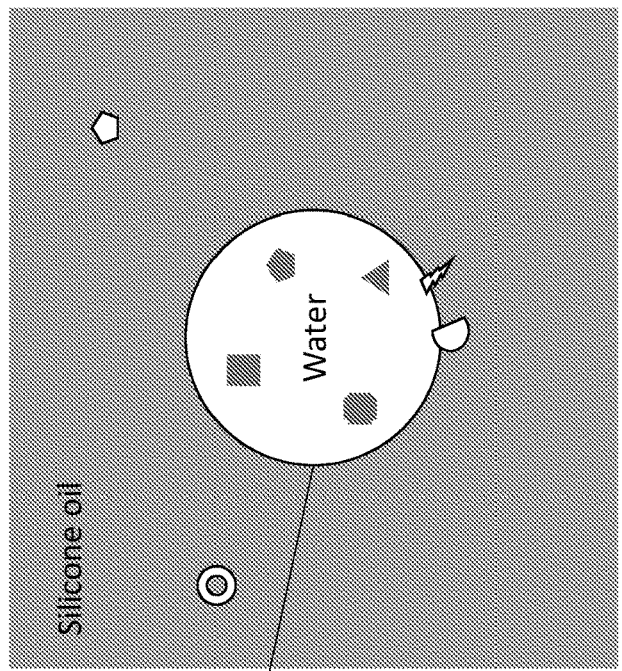
FIG. 1A-1B illustrates exemplary stable water-in-silicone (W/O) emulsions comprising an emulsifier, a cell membrane fluidity enhancing agent, a fatty acid, a preservative, a bioactive agent, a pH buffering system, an antioxidant, and a tocopherol.
Figure 1B:
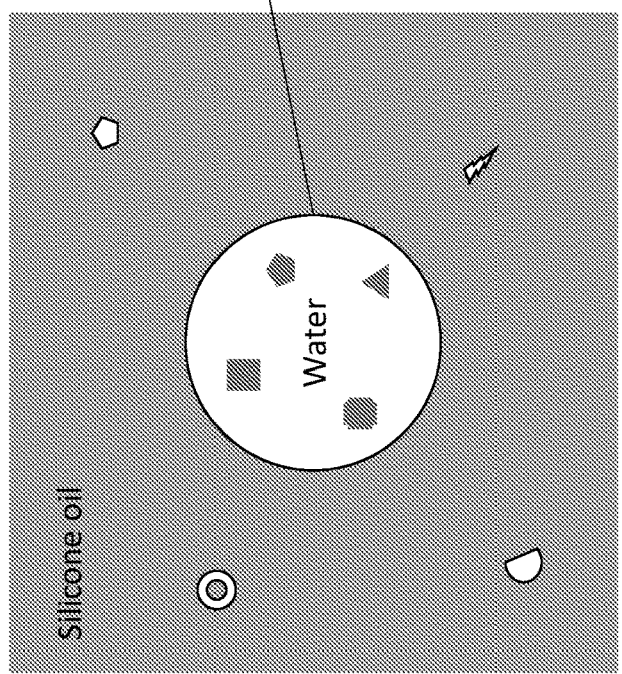
Figure 2A:
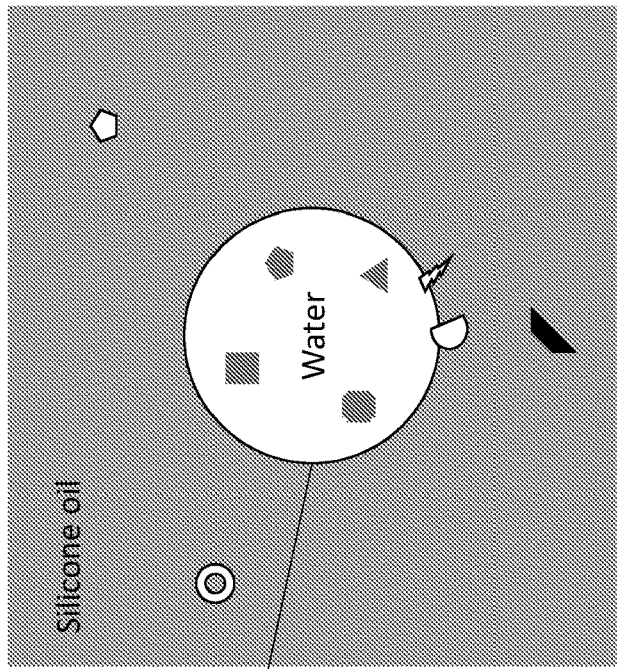
FIG. 2A-2B illustrates an exemplary stable water-in-silicone (W/O) emulsion comprising an emulsifier, a cell membrane fluidity enhancing agent, a fatty acid, a preservative, a bioactive agent, a pH buffering system, an antioxidant, a tocopherol, and an active agent.
Figure 2B:
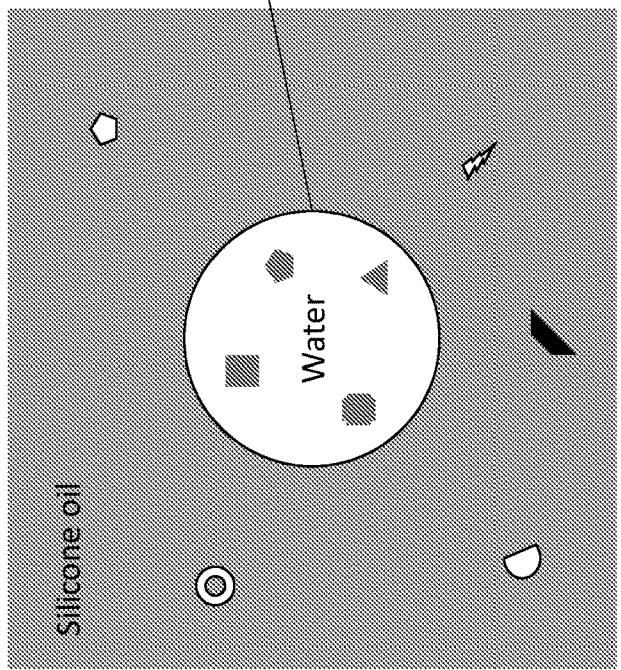

Certain exemplary embodiments will now be described to provide an overall understanding of the principles of the compositions, methods, and kits disclosed herein. One or more examples of these embodiments are illustrated in the accompanying drawings. Those skilled in the art will understand that the compositions, methods, and kits specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

The compositions provided herein are stable emulsions that are in the form of a relatively viscous, lubricious liquid, lotion, ointment, or cream. The compositions are stable as emulsions through expiry and can remain stable after application for up to about one week. The compositions can be used for a variety of purposes, as described herein, including for topical application, rectal application, and vulvovaginal application. Further, the compositions can be used with or without an active and/or bioactive agent. More particularly, provided herein, inter alia, are compositions comprising a water-in-silicone (W/O) emulsion, wherein the emulsion has a sterol at a concentration from about 0.1% to about 4% by weight, of the total weight of the composition. Also provided herein, are methods for preventing or treating vulvovaginal and other conditions (e.g., for rectal utility, dermatological utility, sunscreens, transdermal drug delivery, or ophthalmic utility) of a subject in need thereof, including applying the compositions (e.g., the emulsion comprising a sterol at a concentration from about 0.1% to about 4% by weight, of the total weight of the composition), and kits including the composition and reagents. Although the disclosure often refers to composition being useful to treat vulvovaginal indications, it is understood that this is one of many exemplary uses of the compositions disclosed herein. One skilled in the art will understand that the described compositions have utility beyond vulvovaginal applications, as described herein.

Definitions

The following definitions are included for the purpose of understanding the present subject matter and for constructing the appended patent claims. Abbreviations used herein have their conventional meaning within the chemical and biological arts.

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive. Unless specifically stated or obvious from context, as used herein, the terms "a," "an," and "the" are understood to be singular or plural.

The term "about" when used in reference to numerical ranges, cutoffs, or specific values is used to indicate that the recited values may vary by up to as much as 25% from the listed value. As many of the numerical values used herein are experimentally determined, it should be understood by those skilled in the art that such determinations can, and often times will, vary among different experiments. The values used herein should not be considered unduly limiting by virtue of this inherent variation. The term "about" is used to encompass variations of ±25% or less, variations of ±20% or less, variations of 10% or less, variations of ±5% or less, variations of ±1% or less, variations of ±0.5% or less, or variations of ±0.1% or less from the specified value. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

As used herein, "administering to said subject" and similar terms indicate a procedure by which the described vulvovaginal compositions are introduced into, instilled into, implanted in, applied into, or applied onto a subject such that target cells, tissues, mucosa, or segments of the body of the subject are contacted with the composition.

The term "administering," as used herein, refers to any mode of transferring, delivering, introducing, or transporting an agent, for example, to a subject in need of treatment for a disease or condition. Such modes include, but are not limited to, oral, topical, intravenous, vaginal, mucosal, intraperitoneal, intramuscular, intradermal, intranasal, and subcutaneous administration.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

As used herein, the term "emulsion" refers to a liquefied mixture that contains at least two distinguishable substances (or "phases") that will not readily mix and dissolve together. As used herein, a "emulsion" comprises a "continuous" phase (or "matrix"), which holds therein discontinuous droplets, bubbles, and/or particles of the other phase or substance. The term emulsion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "emulsion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, an emulsion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

As used herein, the term "stable" or "stability" refers to the water-in-silicone emulsion as described herein. Stability can refer to the ability of the emulsion to resist change in its properties over time under appropriate storage conditions. For example, the stability may typically mean that the composition does not phase separate when stored at room temperature (e.g., approximately between 20° C. to 25° C.) for at least 1 month, or when stored in its final packaging at room temperature (e.g., approximately between 20° C. to 25° C.) for at least 12 months. Other exemplary characteristics of stability include the stability of the final packaged product in terms of expiry. For example, the stability may mean that the product constituents (e.g. active or inactive ingredients) have not changed, degraded, or decomposed, the product properties (e.g. emulsion stability, zero-rate viscosity) as defined on its Certificate of Analysis have not changed, the product preservation system remains functional, or any combination thereof. The stability of emulsions can be characterized using techniques described herein, including for example, light scattering, optical microscopy, freeze-thaw cycling, centrifugation, and rheology.

Also, as used herein "stable" or "stability" refers to the composition comprising the water-in-silicone emulsion described herein (e.g., the composition comprising the emulsion and additional agents described herein; "stable composition"). For example, the composition may include carrier(s) and/or other material(s) suitable for the composition to comprise a variety of active agents (e.g. active ingredients), and in which the active agents will be stable for an extended period of time as described herein. In addition, the active agent according to some embodiments should be stable for a period of time in the composition as described herein.

As used in the context of the composition of the present disclosure the term "stable" means physical and chemical stability. Chemical stability refers to chemical changes to an active or inactive agent itself (e.g., degradation of the agents, oxidation of the agents). In embodiments of the present disclosure, storage or shelf-life of a composition is a measure of chemical stability. Physical stability relates to mechanical properties, physical state (e.g., crystallinity, crystal structure), and active agent (or drug) release properties.

The stability is measured after storing the composition of the current disclosure at temperature and relative humidity (RH) conditions of about 25° C./60% RH to about 40° C./75% RH. Accelerated and real time testing of shelf-life of the composition is performed in order to confirm the shelf-life and set the product expiry. In addition, the shelf-life of the composition is also tested under expected packaging conditions.

The stability of the composition should be understood as meaning maintenance of the homogeneous appearance of the composition, without phase separation, precipitation or flocculation of the particles, for at least 6 months at 25° C. In other embodiments, the composition is stable for at least 9 months, at least 12 months, at least 18 months, or at least 24 months at 25° C.

As used herein, the term, "cream" may refer to a thick (high zero-rate viscosity) liquid, semi-liquid, or semi-solid formulation that may be used for therapeutic treatment of a disease, syndrome, or condition (i.e., a vulvovaginal disease, syndrome or condition).

As used herein, the term, "lotion" may refer to a moderately thick (moderate zero-rate viscosity) liquid, semi-liquid, or semi-solid formulation that may be used for therapeutic treatment of a disease, syndrome, or condition (i.e., a vulvovaginal disease, syndrome or condition).

As used herein, the term "ointment" may refer to a highly viscous liquid or semi-liquid formulation that may be used for therapeutic treatment of a disease, syndrome, or condition (i.e., a vulvovaginal disease, syndrome or condition).

"Liquid" as used herein is a dosage form consisting of a composition in its liquid state. A liquid is pourable; it flows and conforms to its container at room temperature. Liquids display Newtonian or pseudoplastic flow behavior. In embodiments, a "semi-liquid" or "semi-solid" as used herein may have properties of both a liquid and another formulation (i.e., a dispersion, a suspension, an emulsion, a lotion, a cream and the like).

The term "moisturizing," as used herein, refers to improving hydration of a surface, such that water-binding capacity of the surface increases. The term "moisturize" or derivatives thereof, relates to the conversion or enhancement of the water contents of surfaces of a subject.

As used herein, "zero-rate viscosity" refers to a fluid or semi-solid's resistance to flow when the shear rate approaches zero.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

By "ameliorate" is meant decrease, suppress, attenuate, diminish, arrest, or stabilize the development or progression of a disease or condition such as, for example, a pseudo-allergic-type reaction.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

The term "around" when used in reference to the site of administration of the described vulvovaginal compositions should be understood by those skilled in the art to mean administered to the anatomical area of interest within the limits of traditionally practiced procedures. For example, administration "around" the relevant anatomical site refers to a location that is not directly within or on the site, but sufficiently close to the site to provide a physiological or therapeutically relevant effect thereon. Those of ordinary skill in the art can readily determine the maximum distance from a given anatomical site that will be sufficient to provide a physiological or therapeutically relevant effect using a vulvovaginal composition according to the present disclosure.

"Pharmaceutically acceptable" refers to those properties and substances which are acceptable to the patient from a pharmacological/toxicological point of view and to the manufacturing pharmaceutical chemist from a physical/chemical point of view regarding composition, formulation, stability, patient acceptance, and bioavailability.

"Pharmaceutically acceptable excipient" and "pharmaceutically acceptable carrier" refer to a substance that aids the administration of an active agent to a subject, or aids absorption by a subject, or improves stability or other properties of the active agent, and can be included in the compositions of the present invention without causing a significant adverse toxicological effect on the patient. Unless indicated to the contrary, the terms "active agent," "active ingredient," "therapeutically active agent," "therapeutic agent," "bioactive agent" and like are used synonymously. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the terms "active agent," "active ingredient," "therapeutically active agent," "therapeutic agent," "bioactive agent" mean "possessing biological activity," such as a biochemical, pharmacological or a therapeutic activity. In some embodiments, the bioactivity is providing symptom relief, treating underlying pathophysiology or infection of the vulvovaginal anatomy, or prophylactically protecting the vulvovaginal anatomy in a subject. In certain embodiments, the bioactivity is enhancement of skin function and/or effect on skin homeostasis. In other examples, the bioactivity is enhancement of the rectal system and anatomy. In yet other examples, the bioactivity is enhancement of the ophthalmic system and anatomy. Also, as provided, the bioactivity is for the treatment or prevention of sun damage (e.g., sunscreen).

In certain embodiments, the biological activity is, without limitation, analgesic, antifungal, antiviral, anti-infective, anti-inflammatory, antineoplastic, immunostimulating, immunosuppressing, immunomodulating, endocrine modulating, enhancement of cell viability, cell membrane fluidizing, antioxidative, oxygen carrier, contraceptive, cell recruitment, cell attachment, angiogenesis, wound healing activity, mobilization of host stem or progenitor cells, cellular proliferation, stimulation of cell migration to injury sites, amelioration of cell and tissue fibrosis, or any combination thereof.

"Therapeutically effective dose" refers to an amount of a composition, as described herein, effective to achieve a particular physiological, biological or therapeutic result such as, but not limited to, the physiological, biological or therapeutic results disclosed, described, or exemplified herein. These physiological, biological or therapeutic results include, but are not limited to, restoring the pH, providing lubrication, promoting healthy flora, or eliminating infections (e.g., restoring pH of the vagina, providing lubrication to the vagina, promoting healthy flora, eliminating infections, or providing contraception). The therapeutically effective dose may vary according to factors such as the disease state, age, sex, and weight of the individual, as well as, the ability of the composition to cause the desired response in a subject. Such results may include, but are not limited to, providing symptom relief, treating underlying pathophysiology, or prophylactically protecting the vagina, as determined by any means suitable in the art.

The terms "treat," "treating" or "treatment" refer to any success or indicia of success in the attenuation or amelioration of an infection, pathology or condition, including any objective or subjective parameter such as abatement, abrogation, remission, diminishing of symptoms or making the infection, pathology, or condition more tolerable to the patient, slowing the disease progression, making the condition less debilitating, or improving a subject's physical or mental well-being. The treatment may be assessed by objective or subjective parameters; including the results of a physical examination.

As used herein, "prophylactically protect" or "prophylactically protecting" means to treat a condition (e.g., a vulvar or vaginal condition) in a preventative manner.

As used herein, "incorporated within" means that the emulsifier, the cell membrane fluidity enhancing agent, the fatty acid, the preservative, and at least one of, the bioactive agent, the pH buffering system, the viscosity enhancing agent, the antioxidant, the tocopherol, the ceramide, the active agent, or any combination thereof, are at least partially covered by, contained within, dispersed within, distributed within, encased within, or entrapped by the water and silicone emulsion. Depending on the type of constituent, excipient, or agent, the constituent, excipient, or agent may be located in the aqueous phase, the silicone phase, or both.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Compositions

The present disclosure provides compositions comprising a water-in-silicone (W/O) emulsion comprising a cell membrane fluidity enhancing agent. In embodiments, the cell membrane fluidity enhancing agent is at a concentration from about 0.1% to about 4% by weight, of the total weight of the composition.

In embodiments, the compositions disclosed herein are stable, water and silicone emulsions that include, but are not limited to, creams, lotions, ointments, moisturizers, or personal lubricants.

Suitable water and silicone emulsions include, but are not limited to, water-in-silicone (W/O), silicone-in-water (O/W) or water-in-silicone-in-water (W/O/W). In some embodiments, the water and silicone emulsion is a W/O emulsion. In preferred examples, a suitable emulsion is a water-in-silicone (W/O) emulsion. For example, without intent to be limiting, W/O emulsions can have an aqueous phase comprising up to 50% by weight of water, inclusive, and a silicone phase comprising between 20% by weight and 95% by weight of silicone, inclusive.

In some examples, the water-in-silicone emulsion comprises a silicone phase, wherein the silicone phase comprises a silicone oil, a silicone wax, a silicone gum, or any combination thereof.

When creating a water-in-silicone emulsion, a number of silicone oils, silicone gums, or silicone waxes may be selected from those known in the art. For the purposes of this disclosure, suitable silicone oils include, but are not limited to, dimethicone, cyclomethicone, caprylyl methicone, cyclopentasiloxane, cyclohexasiloxane or any combination thereof. For the purposes of this disclosure, suitable silicone gums include, but are not limited to, dimethiconol. For the purposes of this disclosure, suitable silicone waxes include, but are not limited to, stearyl dimethicone.

In some embodiments, the dispersant phase (e.g., the phase used to disperse small particles or droplets) may be stabilized to create a stable emulsion. Exemplary agents used to stabilize to create a stable emulsion include, but are not limited to, emulsifiers and co-emulsifiers. Suitable emulsifiers and co-emulsifiers for stabilizing the resulting emulsion (e.g., liquid-liquid droplets) include, but are not limited to, a sterol, a sterol derivative, cholesterol, cholesterol derivatives, glyceryl stearate, glyceryl monostearate, sorbitan monolaurate, sorbitan monopalmitate, sorbitan monostearate, sorbitan tristearate, sorbitan monooleate, sorbitan trioleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, polyoxyethylene monolaurate, polyoxyethylene monostearate, polyoxyethylene monopalmitate, polyoxyethylene monooleate, lecithin, PEG/PPG-18/18 dimethicone, cetyl PEG/PPG-10/1 dimethicone, dimethicone copolyol, octyldodecanol, poly(vinyl alcohol), Pluronic, Poloxamer, Carbomer, isopropyl myristate, or any combination thereof.

In some examples, the compositions described herein can in include one or more (e.g., at least one) cell membrane fluidity enhancing agents to enable (e.g., promote) increased cell membrane fluidity, increased cellular penetration, increased absorption of desired constituents, excipients or agents, increased lubrication and moisturization, or any combination thereof. Suitable cell membrane fluidity enhancing agents include, but are not limited to, sterols (e.g., steroid alcohols). Sterols are a subgroup of steroids with a hydroxyl group at the 3-position of the A-ring. They are amphipathic lipids synthesized from acetyl-coenzyme A. The sterol chemical structure is depicted below:

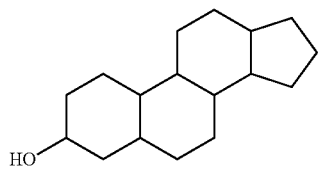 [SMILES: OC1CCC2C(CCC3C4CCCC4CCC23)C1]

The one or more cell membrane fluidity enhancing agents can be incorporated within the emulsion. In some embodiments, the one or more cell membrane fluidity enhancing agents are incorporated within the aqueous phase of the emulsion. In other embodiments, the one or more cell membrane fluidity enhancing agents are incorporated within the silicone phase of the emulsion. In yet other embodiments, the one or more cell membrane fluidity enhancing agents are incorporated within both the aqueous phase and the silicone phase of the emulsion.

In some embodiments, the cell membrane fluidity enhancing agent can be formulated to comprise up to 0.1% by weight, inclusive, of the composition. In some embodiments, the cell membrane fluidity enhancing agent can be formulated to comprise up to 0.25% by weight, inclusive, of the composition. In some embodiments, the cell membrane fluidity enhancing agent can be formulated to comprise up to 0.5% by weight, inclusive, of the composition. In some embodiments, the cell membrane fluidity enhancing agent can be formulated to comprise up to 1% by weight, inclusive, of the composition. In some embodiments, the cell membrane fluidity enhancing agent can be formulated to comprise up to 1.5% by weight, inclusive, of the composition. In some embodiments, the cell membrane fluidity enhancing agent can be formulated to comprise up to 2% by weight, inclusive, of the composition. In some embodiments, the cell membrane fluidity enhancing agent can be formulated to comprise up to 2.5% by weight, inclusive, of the composition. In some embodiments, the cell membrane fluidity enhancing agent can be formulated to comprise up to 3% by weight, inclusive, of the composition. In some embodiments, the cell membrane fluidity enhancing agent can be formulated to comprise up to 3.5% by weight, inclusive, of the composition. In some embodiments, the cell membrane fluidity enhancing agent can be formulated to comprise up to 4% by weight, inclusive, of the composition. In some embodiments, the cell membrane fluidity enhancing agent can be formulated to comprise up to 4.5% by weight, inclusive, of the composition. In some embodiments, the cell membrane fluidity enhancing agent can be formulated to comprise up to 5% by weight, inclusive, of the composition. In some embodiments, the cell membrane fluidity enhancing agent can be formulated to comprise up to 5.5% by weight, inclusive, of the composition.

Throughout the present disclosure, the phrase "the cell membrane fluidity enhancing agent" can refer to more than one cell membrane fluidity enhancing agent if more than one such agent is present in the composition. For example, when only one cell membrane fluidity enhancing agent is incorporated within the emulsion, a reference to "50% by weight of the cell membrane fluidity enhancing agent" means that there is 50% of the sole cell membrane fluidity enhancing agent present. When more than one cell membrane fluidity enhancing agent is incorporated within the emulsion, language referring to "50% by weight of the cell membrane fluidity enhancing agent," means that 50% of the total complement of cell membrane fluidity enhancing agents is incorporated within the emulsion. Thus, if the composition includes 1 mg of a first cell membrane fluidity enhancing agent and 1 mg of a second cell membrane fluidity enhancing agent, then "50% by weight of the cell membrane fluidity enhancing agent" can mean that 50% of the total complement of 2 mg of cell membrane fluidity enhancing agents is incorporated within the emulsion.

The term "sterol" as used herein may refer to natural or synthetic plant or animal sterols. Exemplary sterols include cholesterol, cholesterol derivatives, phytosterols, or any combination thereof. Additional sterols include diosgenin, stigmastanol, tigogenin, α-sitosterol, β-sitosterol, stigmasterol, ergosterol, campesterol, oleanoic acids, soyasapogenols (e.g., soyasapogenol A or soyasapogenol B), protoascigenin, and protopanaxadiols. In some embodiments, the sterol is cholesterol. When the sterol is cholesterol, its physiochemical and biochemical properties enable it to uniquely and simultaneously function as a cell membrane fluidity enhancing agent, as an emulsifier that plays a critical role in stabilizing the water-in-silicone droplet interface, and as a bioactive agent.

In other examples, the compositions described herein can include one or more (e.g., at least one) fatty acids. Fatty acids are carboxylic acids with a long aliphatic chain, which is either saturated or unsaturated. Most naturally occurring fatty acids have an unbranched chain of an even number of carbon atoms, e.g., from 4 to 28 carbon atoms. In embodiments, the fatty acids may facilitate cellular interactions with the formulation. Suitable fatty acids include, but are not limited to, caprylic acid, lauric acid, myristic acid, caproleic acid, lauroleic acid, myristoleic acid, palmitoleic acid, oleic acid, stearic acid, palmitic acid, linoleic acid, arachidonic acid, stearidonic acid, docosahexaenoic acid (DHA), eicosapentaenoic acid (EPA), or any combination thereof.

The one or more fatty acids can be incorporated within the emulsion. In some embodiments, the one or more fatty acids are incorporated within the aqueous phase of the emulsion. In other embodiments, the one or more fatty acids are incorporated within the silicone phase of the emulsion. In yet other embodiments, the one or more fatty acids are incorporated within both the aqueous phase and the silicone phase of the emulsion.

In some embodiments, the fatty acid can be formulated to comprise up to 0.1% by weight, inclusive, of the composition. In some embodiments, the fatty acid can be formulated to comprise up to 0.25% by weight, inclusive, of the composition. In some embodiments, the fatty acid can be formulated to comprise up to 0.5% by weight, inclusive, of the composition. In some embodiments, the fatty acid can be formulated to comprise up to 1% by weight, inclusive, of the composition. In some embodiments, the fatty acid can be formulated to comprise up to 1.5% by weight, inclusive, of the composition. In some embodiments, the fatty acid can be formulated to comprise up to 2% by weight, inclusive, of the composition. In some embodiments, the fatty acid can be formulated to comprise up to 2.5% by weight, inclusive, of the composition. In some embodiments, the fatty acid can be formulated to comprise up to 3% by weight, inclusive, of the composition. In some embodiments, the fatty acid can be formulated to comprise up to 4% by weight, inclusive, of the composition. In some embodiments, the fatty acid can be formulated to comprise up to 5% by weight, inclusive, of the composition. In some embodiments, the fatty acid can be formulated to comprise up to 6% by weight, inclusive, of the composition. In some embodiments, the fatty acid can be formulated to comprise up to 8% by weight, inclusive, of the composition. In some embodiments, the fatty acid can be formulated to comprise up to 10% by weight, inclusive, of the composition.

Throughout the present disclosure, the phrase "the fatty acid" can refer to more than one fatty acid if more than one such agent is present in the composition. For example, when only one fatty acid is incorporated within the emulsion, a reference to "50% by weight of the fatty acid" means that there is 50% of the sole fatty acid present. When more than fatty acid is incorporated within the emulsion, language referring to "50% by weight of the fatty acid" means that 50% of the total complement of fatty acids is incorporated within the emulsion. Thus, if the composition includes 1 mg of a first fatty acid and 1 mg of a second fatty acid, then "50% by weight of the fatty acid" can mean that 50% of the total complement of 2 mg of fatty acids is incorporated within the emulsion.

In other examples, the phrase "the fatty acid" can refer to more than one fatty acid derivative if more than one such agent is present in the composition. Suitable fatty acid derivatives include, but are not limited to, a caprylic acid derivative, a lauric acid derivative, a myristic acid derivative, a caproleic acid derivative, a lauroleic acid derivative, a myristoleic acid derivative, a palmitoleic acid derivative, an oleic acid derivative, a stearic acid derivative, a palmitic acid derivative, a linoleic acid derivative, an arachidonic acid derivative, a stearidonic acid derivative, or any combination thereof.

In embodiments, the disclosed compositions can include one or more preservatives. The preservatives, for example, may be used to control stability and expiry of the formulation, where stability and expiry are evaluated by methods known to those skilled in the art. Suitable preservatives include, but are not limited to, sorbic acid, potassium sorbate, boric acid, sodium borate, benzoic acid, sodium benzoate, benzalkonium chloride, benzethonium chloride, EDTA, parabens, or any combination thereof.

The one or more preservatives can be incorporated within the composition comprising the emulsion. In some embodiments, the one or more preservatives are incorporated within the aqueous phase of the emulsion. In other embodiments, the one or more preservatives are incorporated within the silicone phase of the emulsion. In yet other embodiments, the one or more preservatives are incorporated within both the aqueous phase and the silicone phase of the emulsion.

In some embodiments, the preservative can be formulated to comprise up to 0.01% by weight, inclusive, of the emulsion. In some embodiments, the preservative can be formulated to comprise up to 0.025% by weight, inclusive, of the composition. In some embodiments, the preservative can be formulated to comprise up to 0.05% by weight, inclusive, of the composition. In some embodiments, the preservative can be formulated to comprise up to 0.1% by weight, inclusive, of the composition. In some embodiments, the preservative can be formulated to comprise up to 0.2% by weight, inclusive, of the composition. In some embodiments, the preservative can be formulated to comprise up to 0.5% by weight, inclusive, of the composition. In some embodiments, the preservative can be formulated to comprise up to 1% by weight, inclusive, of the composition. In some embodiments, the preservative can be formulated to comprise up to 2% by weight, inclusive, of the composition. In some embodiments, the preservative can be formulated to comprise up to 4% by weight, inclusive, of the composition.

Throughout the present disclosure, the phrase "the preservative" can refer to more than one preservative if more than one such agent is present in the composition. For example, when only one preservative is incorporated within the emulsion, a reference to "50% by weight of the preservative" means that there is 50% of the sole preservative present. When more than preservative is incorporated within the emulsion, language referring to "50% by weight of the preservative" means that 50% of the total complement of preservatives is incorporated within the emulsion. Thus, if the composition includes 1 mg of a first preservative and 1 mg of a second preservative, then "50% by weight of the preservative" can mean that 50% of the total complement of 2 mg of preservatives is incorporated within the emulsion.

The disclosed compositions can include bioactive agents. In embodiments, the bioactive agents may affect the biochemistry or cellular physiology of the desired condition (e.g., vulvar or vaginal anatomy.) Suitable bioactive agents include, but are not limited to, glycogen, cholesterol, lactic acid, lactate salts, tocopherols, or any combination thereof. Additional bioactive agents are described in detail below.

Throughout the present disclosure, the phrase "the bioactive agent" can refer to more than one bioactive agent if more than one such agent is present in the composition. For example, one or more bioactive agents can be incorporated within the emulsion. In some embodiments, the one or more bioactive agents are incorporated within the aqueous phase of the emulsion. In other embodiments, the one or more bioactive agents are incorporated within the silicone phase of the emulsion. In yet other embodiments, the one or more bioactive agents are incorporated within both the aqueous phase and the silicone phase of the emulsion.

In some examples, bioactive agent can be used in the amount of about 0.01% by weight to about 100% by weight, based on the total weight of the composition. In other examples, the active agent can be used in amount from about 0.01% by weight to about 90% by weight, from about 0.01% by weight, to about 80% by weight, from about 0.01% by weight to about 70% by weight, from about 0.01% by weight to about 60% by weight, from about 0.01% by weight to about 50% by weight, from about 0.01% by weight to about 40% by weight, from about 0.01% by weight to about 30% by weight, from about 0.01% by weight to about 20% by weight, from about 0.01% by weight, to about 10% by weight, from about 0.01% by weight to about 1% by weight, or from about 0.01% by weight to about 0.1% by weight of the composition.

In embodiments, the disclosed composition can include one or more pH buffering systems. For example, the pH buffering systems may be capable of restoring the physiological pH (e.g., of the vagina). Suitable pH buffering systems include, but are not limited to, lactic acid and salts of lactic acid. In some embodiments, the pH buffering system is lactic acid and sodium lactate. In other embodiments, the pH buffering system is lactic acid and calcium lactate. Further, the composition (e.g., a vulvovaginal composition) can have a pH of 3.8 and the pH buffering system can have a buffering capacity within the range of 3.5-4.2.

In examples, the present disclosure includes compositions (e.g., emulsion) having a pH buffering system comprising one or more pH adjusting agents. The pH adjusting agent may be, for example, sodium hydroxide, hydrochloric acid, citric acid, malic acid, tartaric acid, acetic acid, phosphoric acid, maleic acid, glycine, sodium lactate, lactic acid, sodium citrate, ascorbic acid, sodium acetate, acetic acid, sodium bicarbonate, sodium carbonate, carbonic acid, sodium succinate, succinic acid, sodium benzoate, benzoic acid, sodium phosphates, tris(hydroxymethyl)aminomethane, histidine, histidine hydrochloride, or any combination(s) thereof.

Compounds useful as pH adjusting agents include, but are not limited to, boric acid, sodium borate, sodium phosphate (including mono-, di-, tri-basic phosphate, and mixtures thereof). Any other physiologically relevant buffers can be used to stabilize the pH level of the composition by conferring physiological pH approved for medicines. Since said buffers are just examples and these buffers are well known in the field, a person skilled in the art can choose proper buffers that can be used for the composition of the present disclosure.

In examples, the pH of the formulation is from about 2 to about 9. In other examples, the pH is in a range from about 3 to 9, or from about 4 to 9, or from about 5 to 9, or from about 6 to 9, or from about 7 to 9, or from about 8 to 9. In other examples, the pH is in a range from about 3 to 8, or from about 4 to 8, or from about 5 to 8, or from about 6 to 8, or from about 7 to 8. In other examples, the pH is in a range from about 3 to 7, or from about 4 to 7, or from about 5 to 7, or from about 6 to 7. In other examples, the pH is in a range from about 3 to 6, or from about 4 to 6, or from about 5 to 6.

Also as described herein, the disclosed compositions can include one or more viscosity enhancing agents, e.g., to obtain desired mechanical properties. In some examples, the mechanical properties can be measured by rheological methods known by those skilled in the art. Suitable viscosity enhancing agents include, but are not limited to, hydroxymethyl cellulose, hydroxyethyl cellulose, hydroxypropyl cellulose, hydroxypropylmethyl cellulose, carboxymethylcellulose, ethyl cellulose, hyaluronic acid, sodium hyaluronate, Carbomer, Carbopol, poly(acrylic acid), polycarbophil, guar gum, xanthan gum, or any combination thereof.

In embodiments, the zero-rate viscosity of the stable water-in-silicone emulsion can be between 100 Pa-s and 1000 kPa-s. For determination of the zero-rate viscosity of the emulsion, suitable characterization methods include, but are not limited to, rheometry and viscometry.

Throughout the present disclosure, the phrase "the viscosity enhancing agent" can refer to more than one viscosity enhancing agent if more than one such agent is present in the composition. For example, one or more viscosity enhancing agents can be incorporated within the emulsion. In some embodiments, the one or more viscosity enhancing agents are incorporated within the aqueous phase of the emulsion. In other embodiments, the one or more viscosity enhancing agents are incorporated within the silicone phase of the emulsion. In yet other embodiments, the one or more viscosity enhancing agents are incorporated within both the aqueous phase and the silicone phase of the emulsion.

The disclosed compositions can include one or more antioxidants to enhance formulation stability, affect the cellular physiology, or any combination thereof. Suitable antioxidants include, but are not limited to, ascorbic acid, sodium ascorbate, a polyphenol, or any combination thereof.

Throughout the present disclosure, the phrase "the antioxidant" can refer to more than one antioxidant if more than one such agent is present in the composition. For example, one or more antioxidants can be incorporated within the emulsion. In some embodiments, the one or more antioxidants are incorporated within the aqueous phase of the emulsion. In other embodiments, the one or more antioxidants are incorporated within the silicone phase of the emulsion. In yet other embodiments, the one or more antioxidants are incorporated within both the aqueous phase and the silicone phase of the emulsion.

The disclosed compositions can include one or more tocopherols to affect the cellular physiology, lubrication, or any combination thereof. Suitable tocopherols include, but are not limited to, alpha-tocopherol, vitamin E, vitamin E-TPGS, tocopheryl acetate, or any combination thereof. Tocopherols (e.g. vitamin E) can provide lubricity, antioxidant properties, or any combination thereof.

Throughout the present disclosure, the phrase "the tocopherol" can refer to more than one tocopherol if more than one such agent is present in the composition. For example, one or more tocopherols can be incorporated within the emulsion. In some embodiments, the one or more tocopherols are incorporated within the aqueous phase of the emulsion. In other embodiments, the one or more tocopherols are incorporated within the silicone phase of the emulsion. In yet other embodiments, the one or more tocopherols are incorporated within both the aqueous phase and the silicone phase of the emulsion.

The disclosed compositions can include one or more active agents to provide symptom relief, treat underlying pathophysiology or infection, or prophylactically protect the anatomy (e.g., the vagina) of the subject. Suitable classes of active agents include, but are not limited to, antifungals, antibiotics, spermicides, estrogens, estrogen derivatives, progesterone, progesterone derivatives, estrogen precursors, steroids, anti-inflammatories, antivirals/antiretrovirals (e.g. CCR5 antagonists, nucleoside reverse transcriptase inhibitors (NRTIs), non-nucleoside reverse transcriptase inhibitors (NNRTIs), protease inhibitors (PIs), fusion inhibitors, integrase inhibitors, post-attachment inhibitors, pharmacokinetic enhancers), or any combination thereof. Suitable active agents include, but are not limited to, miconazole, metronidazole, clotrimazole, estradiol, prasterone, nonoxynol-9, or any combination thereof. In some embodiments, the active agent is miconazole. In some embodiments, the active agent is metronidazole. In some embodiments, the active agent is clotrimazole. In some embodiments, the active agent is estradiol. In some embodiments, the active agent is prasterone. In some embodiments, the active agent is nonoxynol-9.

The disclosed compositions can include one or more active agents to treat or protect the skin of the subject. Suitable classes of active agents include, but are not limited to, antibiotics, antimicrobials, antifungals, antiseptics, local anesthetics, analgesics, anti-inflammatories, immunosuppressants, steroids, corticosteroids, calcineurin inhibitors, PDE4 inhibitors, salicylic acid, retinoids, antihistamines, benzoyl peroxide, nanocrystalline silver, or any combination thereof.

Exemplary antibiotics include, but are not limited to amoxicillin, doxycycline, cephalexin, ciprofloxacin, clindamycin, metronidazole, azithromycin, sulfamethoxazole/trimethoprim, amoxicillin/clavulanate, and levofloxacin. Additional antibiotcs include Mikacin, Gentamicin, Kanamycin, Neomycin, Netilmicin, Tobramycin, Paromomycin, Streptomycin, Spectinomycin(Bs), Geldanamycin, Herbimycin, Rifaximin, Loracarbef, Ertapenem, Doripenem, Imipenem/Cilastatin, Meropenem, Cefadroxil, Cefazolin, Cephradine, Cephapirin, Cephalothin, Cefalexin, Cefaclor, Cefoxitin Cefotetan, Cefamandole, Roxithromycin, Telithromycin, Spiramycin, Fidaxomicin, Furazolidone, Nitrofurantoin(Bs), Linezolid, Posizoli, Radezolid, Torezolid, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Norfloxacin, Ofloxacin, Trovafloxacin, Minocycline, Oxytetracycline, Tetracycline, Clofazimine, Dapsone, Capreomycin, Cycloserinem Pyrazinamide, Rifampicin, Rifabutin, Rifapentine, Streptomycin, Metronidazole, and Mupirocin Exemplary antimicrobials include, but are not limited to amoxicillin, doxycycline. Cephalexin, ciprofloxacin, clindamycin, metronidazole, azithromycin, sulfamethoxazole/trimethoprim, amoxicillin/clavulanate, and levofloxacin.

Exemplary antifungals include, but are not limited to, miconazole, clotrimazole, amphotericin B, ketoconazole, fluconazole, isavuconazole, itraconazole, posaconazole, voriconazole, anidulafungin, caspofungin, micafungin, and flucytosine.

Exemplary antiseptics include ethanol, sodium hypochlorite, chlorhexidine, hexachlorophene, povidone iodine, sodium hypochlorite, sodium hypochlorite, benzethonium chloride, triclosan, oxychlorosene sodium, benzalkonium chloride, and silver nitrate.

Exemplary local anesthetics include amylocaine, ambucaine, articaine, benzocaine, benzonatate, bupivacaine, butacaine, butanilicaine, chloroprocaine, cinchocaine(INN), cocaine, cyclomethycaine, dibucaine, diperodon, dimethocaine, eucaine, etidocaine, hexylcaine, fomocaine, fotocaine, hydroxyprocaine, isobucaine, levobupivacaine, lidocaine (lignocaine), mepivacaine, meprylcaine, metabutoxycaine, nitracaine, orthocaine, oxetacaine(oxethazaine), oxybuprocaine, paraethoxycaine, phenacaine, piperocaine, piridocain, pramocaine, prilocaine, primacaine, procaine, procainamide, proparacaine, propoxycaine, pyrrocaine, quinisocaine(INN), ropivacaine, trimecaine, tetracaine, tolycaine, and tropacocaine.

Exemplary analgesics include codeine, fentanyl, hydrocodone (Hysingla, Zohydro, Hydrocodone/acetaminophen (Lorcet, Lortab, Norco, Vicodin), Hydromorphone (Dilaudid, Exalgo), Meperidine (Demerol), Methadone (Dolophine, Methadose), Morphine (Kadian, MS Contin, Morphabond), Oxycodone (OxyContin, Oxaydo), Oxycodone and acetaminophen (Percocet, Roxicet), and Oxycodone and naloxone.

Exemplary anti-inflammatories include celecoxib (Celebrex), diclofenac (Cambia, Cataflam, Voltaren-XR, Zipsor, Zorvolex), diflunisal (Dolobid), etodolac (Lodine), ibuprofen (Motrin, Advil), indomethacin (Indocin), ketoprofen (Active-Ketoprofen, ketorolac, nabumetone naproxen (Aleve, Anaprox, Naprelan, Naprosyn), oxaprozin (Daypro), piroxicam (Feldene), salsalate, sulindac, and tolmetin.

Exemplary immunosuppressants include corticosteroids (e.g., prednisone (Deltasone, Orasone), budesonide (Entocort EC), prednisolone, and (Millipred)), Janus kinase inhibitors (e.g. tofacitinib (Xeljanz)), Calcineurin inhibitors, e.g., cyclosporine (Neoral, Sandimmune, SangCya), and tacrolimus (Astagraf XL, Envarsus XR, Prograf), mTOR inhibitors, e.g., sirolimus (Rapamune), and everolimus (Afinitor, Zortress), IMDH inhibitors, e.g., azathioprine (Azasan, Imuran), leflunomide (Arava), and mycophenolate (CellCept, Myfortic), biologics, e.g., abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), and monoclonal antibodies, e.g., basiliximab (Simulect), daclizumab (Zinbryta), and muromonab (Orthoclone OKT3).

Exemplary calcineurin inhibitors include astagraf XL, cyclosporine, cyclosporine ophthalmic, Elidel, Envarsus XR, Gengraf, Hecoria, Neoral, pimecrolimus, Prograf, Protopic, Restasis, Sandimmune, tacrolimus, and tacrolimus ointment.

Exemplary phosphodiesterase 4 (PDE4) inhibitors include Adibendan, Aminophylline, Aminophylline dehydrate, Amipizone, Apremilast, Arofylline, Atizoram, Befuraline, Bemarinone hydrochloride, Bemoradan, Benafentrine, Bucladesine, Buflomedil, Buquineran, CC-1088, Carbazeran, Catramilast, Cilomilast, Cilostamide, Cilostazol, Cipamfylline, Crisaborole, Daxalipram, Denbufylline, Dimabefylline, Diniprofylline, Dipyridamole, Doxofylline, Drotaverine, Dyphylline, Enoximone, Etamiphyllin, Etofylline, Filaminast, Flufylline, Fluprofylline, Furafylline, Imazodan, Imazodan hydrochloride, Inamrinone, Inamrinone lactate, Isbufylline, Lirimilast, Lisofylline, Lomifylline, Medorinone, Metescufylline, Midaxifylline, Milrinone, Milrinone lactate, Motapizone, Nanterinone, Nestifylline, Nitraquazone, Oglemilast, Oglemilast Sodium, Olprinone, Oxagrelate, Oxtriphylline, Papaverine, Papaverine hydrochloride, Papaverine sulfate, Parogrelil, Pelrinone hydrochloride, Pentifylline, Pentoxifylline, Perbufylline, Piclamilast, Pimefylline, Pimobendan, Piroximone, Prinoxodan, Proxyphylline, Pumafentrine, Quazinone, Quazodine, Revamilast, Revizinone, Roflumilast, Rolipram, Ronomilast, Saterinone, Senazodan, Siguazodan, Tetomilast, Tofimilast, Trapidil, Vesnarinone, and Zardaverine.

The disclosed compositions can include one or more active agents to provide symptom relief or treat underlying pathophysiology, or protect the anatomy (e.g., the rectum) of the subject. Suitable classes of active agents include, but are not limited to, vasoconstrictors, anti-inflammatories, steroids, local anesthetics, alpha-adrenergic receptor agonists, onabotulinumtoxinA, calcium channel inhibitors, nitrates, or any combination thereof.

The one or more active agents can be incorporated within the emulsion. In some embodiments, the one or more active agents are incorporated within the aqueous phase of the emulsion. In other embodiments, the one or more active agents are incorporated within the silicone phase of the emulsion. In yet other embodiments, the one or more active agents are incorporated within both the aqueous phase and the silicone phase of the emulsion.

In some embodiments, the active agent can be formulated to be present in an amount typical for such an agent. For example, the agent can be formulated to comprise up to 0.01% by weight, inclusive, of the composition. In some embodiments, the active agent can be formulated to comprise up to 0.025% by weight, inclusive, of the composition. In some embodiments, the active agent can be formulated to comprise up to 0.05% by weight, inclusive, of the composition. In some embodiments, the active agent can be formulated to comprise up to 0.1% by weight, inclusive, of the composition. In some embodiments, the active agent can be formulated to comprise up to 0.2% by weight, inclusive, of the composition. In some embodiments, the active agent can be formulated to comprise up to 0.5% by weight, inclusive, of the composition. In some embodiments, the active agent can be formulated to comprise up to 1% by weight, inclusive, of the composition. In some embodiments, the active agent can be formulated to comprise up to 2% by weight, inclusive, of the composition. In some embodiments, the active agent can be formulated to comprise up to 4% by weight, inclusive, of the composition. In some embodiments, the active agent can be formulated to comprise up to 6% by weight, inclusive, of the composition. In some embodiments, the active agent can be formulated to comprise up to 8% by weight, inclusive, of the composition. In some embodiments, the active agent can be formulated to comprise up to 10% by weight, inclusive, of the composition.

Throughout the present disclosure, the phrase "the active agent" can refer to more than one active agent if more than one such agent is present in the composition. For example, when only one active agent is incorporated within the emulsion, a reference to "50% by weight of the active agent" means that there is 50% of the sole active agent present. When more than active agent is incorporated within the emulsion, language referring to "50% by weight of the active agent" means that 50% of the total complement of active agents is incorporated within the emulsion. Thus, if the composition includes 1 mg of a first active agent and 1 mg of a second active agent, then "50% by weight of the active agent" can mean that 50% of the total complement of 2 mg of active agents is incorporated within the emulsion.

The compositions of the present invention can contain a safe and effective amount of a conditioning agent, for example, humectants, emollients, moisturizers, and skin conditioners. A variety of these materials can be employed and can be present at a level of from about 0.01% to about 80%, more preferably from about 0.1% to about 25%, and still more preferably from about 0.5% to about 10%, by weight of the composition. The exact content (%) of humectants, emollients, moisturizers, and conditioning agents to be used in the compositions will depend on the humectant, emollient, moisturizer, and conditioning agent utilized since such agents vary widely in potency.

Humectants are ingredients that help maintain moisture levels in skin. Humectants include, for example, polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Additional humectants include acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed proteins, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, butylene glycol, sodium pyrollidone carboxylic acid (PCA), sorbitol, sucrose, dextran sulfate (i.e., of any molecular weight), natural moisturizing factors, and/or urea.

Skin conditioners can include, but are not limited to, guanidine, urea, glycolic acid, glycolate salts (e.g., ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, hexanetriol, butanetriol, propylene glycol, butylene glycol, hexylene glycol and the like, polyethylene glycols, propoxylated glycerols, sugars (e.g., melibiose), starches, sugar and starch derivatives (e.g., alkoxylated glucose, fructose, glucosamine), C1-C30 monoesters and polyesters of sugars and related materials, hyaluronic acid, lactamide monoethanolamine, acetamide monoethanolamine, panthenol, dexpanthenol, allantoin, and mixtures thereof. Skin conditioners can also include fatty acids, fatty acid esters, lipids, ceramides, cholesterol, cholesterol esters, bee wax, petrolatum, and mineral oil.

Emulsions can be configured to be administered and/or applied to a subject. Suitable methods of administration include, but are not limited to, being introduced into, instilled into, implanted in, applied into, or applied onto the vulvovaginal anatomy, the rectal anatomy, the skin, or the eye in a subject. For example, in some aspects, the emulsion is configured to be applied into the vagina in a subject. In other aspects, the emulsion is configured to be applied onto and around the vulva in a subject.

Anatomical and physiological interactions, physiological clearance, diffusion, or any combination thereof, can lead to the release of the cell membrane fluidity enhancing agent, the fatty acid and at least one of, the bioactive agent, the pH buffering system, the antioxidant, the tocopherol, the ceramide, the active agent, or any combination thereof, from the stable water-in-silicone emulsion, thus providing a therapeutically effective dose of to the subject.

In some embodiments, the emulsified formulation provides a therapeutically effective dose for up to 2 hours from a single dose. In some embodiments, the emulsified formulation provides a therapeutically effective dose for up to 4 hours from a single dose. In some embodiments, the emulsified formulation provides a therapeutically effective dose for up to 8 hours from a single dose. In some embodiments, the emulsified formulation provides a therapeutically effective dose for up to 12 hours from a single dose. In some embodiments, the emulsified formulation provides a therapeutically effective dose for up to 18 hours from a single dose. In some embodiments, the emulsified formulation provides a therapeutically effective dose for up to 24 hours from a single dose. In some embodiments, the emulsified formulation provides a therapeutically effective dose for up to 48 hours from a single dose. In some embodiments, the emulsified formulation provides a therapeutically effective dose for up to 3 days from a single dose. In some embodiments, the emulsified formulation provides a therapeutically effective dose for up to 5 days from a single dose. In some embodiments, the emulsified formulation provides a therapeutically effective dose for up to 7 days from a single dose. In some embodiments, the emulsified formulation provides a therapeutically effective dose for up to 14 days from a single dose.

In embodiment, the composition can be administered as needed, such as once daily, from two to five times daily, up to two times or up to three times daily, or up to eight times daily. In embodiments, the composition is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In other examples, the composition is administered once a week, or once every two weeks, or once every 3 weeks or once every 4 weeks for at least 1 week, in some embodiments for 1 to 4 weeks, from 2 to 6 weeks, from 2 to 8 weeks, from 2 to 10 weeks, or from 2 to 12 weeks, 2 to 16 weeks, or longer (e.g., 1, 2, 3, 4, 5, 6, 7, 8, 9, 10, 11, 12, 36, 48, or more weeks).

Pharmaceutically acceptable constituents, excipients or agents may also be included in the compositions described herein. In some aspects, the pharmaceutical acceptable agents may stabilize the composition, allow it to be readily administered to the vulvovaginal anatomy (e.g., the vulva, vagina, or both), the rectal anatomy, the skin, or the eye of a subject, increase its ability to provide symptom relief, treat underlying pathophysiology or infection, or prophylactically protect the vagina of a subject, or otherwise make the composition suitable for therapeutic use in a subject. Accordingly, the described composition may further comprise a pharmaceutically acceptable excipient, as would be known to an individual skilled in the relevant art. In view of the inclusion of active agents in some of the described vulvovaginal, rectal, dermatological, or ophthalmic compositions, disclosed herein are also pharmaceutical compositions having a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, a ceramide, and an active agent, as provided herein. The described pharmaceutical compositions may be administered to a subject in order to provide symptom relief, treat underlying pathophysiology or infection, or prophylactically protect the vagina of a subject.

The present disclosure also provides methods comprising combination therapy for the treatment or prevention of the diseases and conditions described herein. As used herein, "combination therapy" or "co-therapy" includes the administration of a composition described herein, e.g., a composition comprising a stable water-in-silicone emulsion having a continuous silicone phase and an aqueous phase, wherein the emulsion comprises a sterol at a concentration from about 0.1% to about 4% by weight, of the total weight of the composition, with at least one additional agent, as disclosed herein, as part of a specific treatment regimen intended to provide the beneficial effect from the co-action of these therapeutic compositions.

In embodiments, the at least one additional agent in combination therapy may be a therapeutic agent or a non-therapeutic agent. The beneficial effect of the combination includes, but is not limited to, pharmacokinetic or pharmacodynamic co-action resulting from the combination of therapeutic compounds and the disclosed composition. The beneficial effect of the combination may also relate to the mitigation of a toxicity, side effect, or adverse event associated with another agent in the combination. "Combination therapy" may be, but generally is not, intended to encompass the administration of two or more of these therapeutic compounds as part of separate monotherapy regimens that incidentally and arbitrarily result in the combinations of the present disclosure.

In the context of combination therapy, administration of the compositions described herein, may be simultaneous with or sequential to the administration of the one or more additional agents. In another aspect, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional agents can be formulated for co-administration with a composition of the present disclosure in a single dosage form, as described herein. The one or more additional agents can be administered separately from the dosage form that comprises the composition of the present disclosure. When the additional agent is administered separately from a composition of the present disclosure, it can be by the same or a different route of administration as the composition of the instant disclosure.

Preferably, the administration of a composition of the present disclosure in combination with one or more additional agents provides a synergistic response in the subject having a disorder, disease or condition of the present disclosure. In this context, the term "synergistic" refers to the efficacy of the combination being more effective than the additive effects of either single therapy alone. The synergistic effect of combination therapy according to the disclosure can permit the use of lower dosages and/or less frequent administration of at least one agent in the combination compared to its dose and/or frequency outside of the combination. The synergistic effect can be manifested in the avoidance or reduction of adverse or unwanted side effects associated with the use of either therapy in the combination alone.

"Combination therapy" also embraces the administration of the composition of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved.

Physical and Chemical Properties of the Water-in-Silicone Emulsion

Droplet Size

In some examples, the emulsion described herein comprises droplets (alternatively, "particles"). The liquid-liquid droplets comprising the emulsified formulation can have a median diameter of up to 250 microns. For example, the droplets can have a median diameter from about 10 to about 250 microns, from about 50 to 250 microns, from about 100 to 250 microns, from about 150 to 250 microns, or from about 200 to 250 microns. In some examples, the droplet/particle is about 10 to about 100,000 nanometers (100 µm) in diameter. For example, the droplet/particle may be about 10, 50, 100, 200, 300, 400, 500, 1000, 10,000, or 100,000 nanometers in diameter. In some embodiments, a device or apparatus may be used to deliver a droplet/particle to the subject.

The droplet size may be analyzed by known methods in the art. Suitable methods of droplet size analysis include, but are not limited to, light microscopy, dynamic light scattering, and laser diffraction.

Methods of Preparing

Also provided herein are methods of preparing the compositions comprising a water-in-oil emulsion. In some examples, the emulsion can be prepared using techniques including, but are not limited to, rotor-stator emulsification, static mixing, or high shear mixing.

In embodiments, the composition is emulsified to form a stable emulsion with the desired droplet size. High-shear devices that may be used include, but are not limited to, IKA Ultra-Turrax disperser, IKA Dispax-Reactor DR and DRS (Dispax-Reactor shear mixers include the DR3-6 with three stages of rotor/stator combinations and the tip speed of the rotor/stator generators may be varied by a variable frequency drive that controls the motor), Silverson mixer (a two-stage mixer, which incorporates a rotor/stator design and has high-volume pumping characteristics similar to centrifugal pump), inline shear mixers by Silverson Corporation (a rotor-stator emulsification approach), jet mixers (venturi-style/cavitation shear mixers), Ultrasonolator by the Sonic Corporation (ultrasonic emulsification approach), microfluidizer shear mixers available by Microfluidics Inc (high-pressure homogenization shear mixers), ultrasonic mixers, and any other available high-shear mixer.

In other embodiments, the composition is emulsified to form a stable emulsion using a static mixer. A static mixer is a precision engineered device for the continuous mixing of fluid materials, without moving components.

Composition, Generally

As described herein, certain aspects of the present invention relate to the use of the compositions to make cosmetics, personal care products, feminine care products, hygiene products, dermatology products, ophthalmic products, pharmaceutical preparations, or medicaments for maintaining healthy skin, skin rejuvenation, restoration of damaged skin including, but not limited to, skin after cosmetic and dermatological procedures, wound healing, treatment of atrophy of any human tissue including vulvovaginal atrophy, and/or other conditions, disorders and diseases of skin and mucosa in humans associated with changes in extracellular matrix components.

This is accomplished by topical application of the composition of the invention to the skin or mucosa of the human needing such treatment. In some limited cases, this can be accomplished by topical administration of the composition of the invention in a human needing such treatment.

Certain aspects of the present invention also relate to methods of using such compositions for the treatment or prevention in dermatological applications, as well as for enhancing wound healing, reducing the atrophy of any human tissue including vulvovaginal atrophy, and for improving other conditions, disorders and diseases of skin and mucosa in humans. These methods generally involve topically applying the composition to the affected skin or the affected anatomy when needed, in the amount and at the frequency best suited for the purpose. Methods of preventing, delaying the onset, or treating a skin or mucosal condition, disorder or disease are also contemplated.

Those skilled in the art will further recognize that the administration of any of the compositions and/or formulations of the invention treats, alleviates, or ameliorates conditions, disorders and diseases of skin and mucosa in humans, for example wounded skin, damaged skin after cosmetic and dermatological procedures, atrophy of skin and mucosa due to other causes than aging (e.g., emotional stress, use of oral contraceptive pills, use of aromatase inhibitors, due to surgery, etc.), and for other conditions, and/or disorders and diseases of skin and mucosa in humans.

Vulvovaginal Compositions

Vulvar and vaginal atrophy (VVA), resulting from the loss of estrogen stimulation on vaginal and vulvar tissue, is a common medical condition in peri- and post-menopausal women. VVA often manifests with discomfort what can be experienced as vaginal dryness, lack of lubrication, rawness, burning, irritation, inflammation, atrophic vaginitis, dyspareunia (pain during sexual intercourse), and pain generally. VVA occurs most often after menopause, but it can also develop during breast-feeding, as a consequence of breast cancer treatment, or at any other time the women's estrogen production declines. Furthermore, recent evidence indicates that women taking oral contraceptives (which can cause a decline in the production of certain sex hormones such as testosterone) may also experience vulvovaginal atrophy. VVA will occur in most post-menopausal women at some point in their lives. There are an estimated 64 million post-menopausal women in the United States, and as many as 32 million women may suffer from VVA symptoms.

Existing non-prescription treatments (e.g., non-hormonal, over-the-counter (OTC) creams, moisturizers, and lubricants) are lacking in several areas, for example, they are not capable of restoring stasis to the anatomy and physiology; they often contain ingredients that are not well-tolerated in the vaginal canal; they are often not isotonic; and they are dramatically inferior to Hormone Replacement Therapies (HRT) in terms of symptom relief and treatment of underlying pathology.

The pathophysiology of VVA is such that the decreasing levels of estrogen associated with peri- and post-menopause cause (1) a thinning of the superficial cells and stratified squamous epithelial cells that line the vaginal mucosa and (2) a decrease in squamous epithelial glycogenation, resulting in a decrease of exfoliated, glycogenated cells. Glycogen is an important biomolecule that is responsible for maintaining vaginal health. The conversion of glycogen to lactic acid by Lactobacilli, the beneficial flora of the vaginal mucosa, is essential for maintaining the healthy, low vaginal pH. In the absence of glycogen, the vaginal pH rises, resulting in a decrease in Lactobacilli and a potential for overgrowth of harmful bacteria that can lead to infection and inflammation. Further, the decline in estrogen levels leads to decreased vulvovaginal blood flow, decrease mucous production, and decreased vaginal lubrication. Thus, provided herein are compositions and methods that address these needs. Provided herein are vulvovaginal compositions (e.g., lubricants, moisturizers, creams) that are non-hormonal, isotonic, long-lasting, capable of slowing the progression of VVA (e.g. by restoring pH balance, providing meaningful lubrication, and providing symptom relief—vaginal dryness—for at least 24 hours from a single application), and comprise only well-tolerated, generally recognized as safe (GRAS) ingredients that are latex and lactobacilli compatible.

Provided herein are compositions, e.g., vulvovaginal compositions. In some embodiments, the vulvovaginal compositions are formulated specifically to not require active agents for the treatment of certain indication. Alternatively, the present disclosure also provides vulvovaginal compositions that are formulated to enable incorporation of active agents. In both cases, the formulation method is selected specifically to exert control over 1) formulation stability, 2) mechanical properties, and 3) therapeutically relevant incorporation of desired constituents, excipients, or agents.

The disclosed vulvovaginal compositions can be administered by application. For example, the vulvovaginal compositions can be applied into the vagina using an applicator known by those skilled in the art. Additionally, the vulvovaginal compositions can be applied onto the vulva by methods known by those skilled in the art. In some embodiments, the vulvovaginal composition can be administered into the vagina. In some aspects, the vulvovaginal composition can be applied into the vagina. In other embodiments, the vulvovaginal composition can be administered onto or around the vulva. In some aspects, the vulvovaginal composition can be applied onto or around the vulva. In other embodiments, the vulvovaginal composition can be administered onto or around vaginal superficial cells. In some aspects, the vulvovaginal composition can be applied onto or around vaginal superficial cells. In yet other embodiments, the vulvovaginal composition can be administered onto or around vaginal squamous epithelial cells. In some aspects, the vulvovaginal composition can be applied onto or around vaginal squamous epithelial cells.

The disclosed vulvovaginal compositions can be used to provide vaginal symptom relief, treat underlying pathophysiology or infection of the vaginal anatomy, or prophylactically protect the vagina in a subject by, for example, administering the composition into the vagina. The disclosed vulvovaginal compositions can be used to provide vulvar symptom relief, treat underlying pathophysiology or infection of the vulvar anatomy, or prophylactically protect the vulva in a subject by, for example, administering the composition onto the vulva.

In embodiments, the vulvovaginal composition can be used to prevent or treat bacterial vaginosis, vulvovaginal atrophy, yeast infections, as sexually transmitted infection (STI) and/or sexually transmitted disease (STD) prophylaxis, as a personal lubricant, a vaginal moisturizer, a local hormone replacement therapy, or as contraception.

Additionally, the disclosed compositions can be used to provide vulvovaginal symptom relief, treat underlying pathophysiology or infection of the vulvovaginal anatomy, or prophylactically protect the vulvovaginal anatomy in a subject. The need for treatment or prophylaxis can arise from a number of conditions, including, but not limited to, menopause, peri-menopause, post-menopause, decrease in estrogen concentration, atrophic vaginitis, vulvar and vaginal atrophy, bacterial vaginosis, vaginal dryness, vaginal itch, vaginal irritation, dyspareunia, bacterial infection, yeast infection, urinary tract infection, need for vaginal lubrication and moisture, sexual intercourse, need for contraceptive prophylaxis, or any combination thereof.

In some examples, the disclosed vulvovaginal compositions can include a bioactive agent. Examples of contemplated bioactive agents include, but are not limited to, glycogen, lactic acid, cholesterol, or any combination thereof.

In some examples, the disclosed vulvovaginal compositions can include an active agent. Examples of contemplated active agents include, but are not limited to, antifungals, antibiotics, spermicides, estrogens, estrogen derivatives, progesterone, progesterone derivatives, estrogen precursors, steroids, anti-inflammatories, antivirals/antiretrovirals (e.g. CCR5 antagonists, nucleoside reverse transcriptase inhibitors (NRTIs) as described herein), non-nucleoside reverse transcriptase inhibitors (NNRTIs), protease inhibitors (PIs) (e.g., atazanavir (Reyataz), darunavir (Prezista), fosamprenavir (Lexiva), indinavir (Crixivan), lopinavir/ritonavir (Kaletra), nelfinavir (Viracept), ritonavir (Norvir), saquinavir (Invirase), tipranavir (Aptivus), atazanavir/cobicistat (Evotaz), and darunavir/cobicistat (Prezcobix)), fusion inhibitors (e.g., T-20 (enfuvirtide, Fuzeon)), integrase inhibitors e.g., raltegravir, dolutegravir, and cabotegravir), post-attachment inhibitors, and pharmacokinetic enhancers.

In embodiments the active agent for the vulvovaginal composition can include a steroidal anti-inflammatory agent. Exemplary steroidal anti-inflammatory bioactive agents include, but are not limited to, corticosteroids such as prasterone, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chloroprednisone acetate, clocortelone, clescinolone, dichlorisone, difluprednate, fluclo-ronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used.

In other embodiments, the active agent comprises a second class of anti-inflammatory agents which is useful in the compositions, and includes the nonsteroidal anti-inflammatory agents. The variety of compounds encompassed by this group are well-known to those skilled in the art.

In one embodiment, the additional agent is an anti-viral agent. Non-limiting examples of anti-viral agents that may be used in combination with a composition as described herein include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime. Combinations of anti-viral agents are also contemplated in the compositions described herein.

In some embodiments, the vulvovaginal composition includes one or more active and/or bioactive agents. In some embodiments, the vulvovaginal composition includes two active agents, for example, estradiol and prasterone. In another example, the vulvovaginal composition includes an active and a bioactive agent, for example, estradiol and glycogen, respectively.

In embodiments, the vulvovaginal composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the vulvovaginal composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes a vulvovaginal composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the vulvovaginal composition including a cell membrane fluidity enhancing agent (e.g., a sterol, wherein exemplary sterols include cholesterol, cholesterol derivatives, phytosterols, or any combination thereof) has a pH of about 3 to about 4.5. In other embodiments, the pH is about 3.8.

In some examples, the vulvovaginal composition including a cell membrane fluidity enhancing agent (e.g., a sterol, wherein exemplary sterols include cholesterol, cholesterol derivatives, phytosterols, or any combination thereof) has an osmolarity of about 280 to about 380 mOsm/kg.

The vulvovaginal composition should have a zero-rate viscosity that is resistant change over time and/or temperature. The terms "viscous," "viscosity", "zero-rate viscosity' and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the vulvovaginal composition has a zero-rate viscosity of about 50 kPa-s to about 1000 kPa-s at 25° C. In examples, the composition has the desired zero-rate viscosity, (e.g., about 200 kPas at 25° C.) for at least 12 months.

In some examples, the vulvovaginal composition including a cell membrane fluidity enhancing agent (e.g., a sterol, wherein exemplary sterols include cholesterol, cholesterol derivatives, phytosterols, or any combination thereof) has a zero-rate viscosity of about 50 kPa-s to about 1000 kPa-s at 25° C.

In some examples, the vulvovaginal composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

Vulvovaginal Methods

Also provided herein are methods for providing vulvovaginal symptom relief, treating underlying pathophysiology or infection of the vulvovaginal anatomy, or prophylactically protecting the vulvovaginal anatomy in a subject comprising administering to a subject any one of the compositions disclosed herein. In some embodiments, the methods for providing vulvovaginal symptom relief, treating underlying pathophysiology or infection of the vulvovaginal anatomy, or prophylactically protecting the vulvovaginal anatomy in a subject can comprise administering to a subject a vulvovaginal composition comprising a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent. In other embodiments, the methods for providing vulvovaginal symptom relief, treating underlying pathophysiology or infection of the vulvovaginal anatomy, or prophylactically protecting the vulvovaginal anatomy in a subject can comprise administering to a subject a vulvovaginal composition consisting of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent. In yet other embodiments, the methods for providing vulvovaginal symptom relief, treating underlying pathophysiology or infection of the vulvovaginal anatomy, or prophylactically protecting the vulvovaginal anatomy in a subject can comprise administering to a subject a vulvovaginal composition consisting essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent.

Dermatological Compositions

Also provided herein are dermatological compositions. The dermatological compositions described herein can be used as a skin protectant or moisturizer. In other examples, the dermatological compositions can be used to treat or prevent eczema, psoriasis, plaque psoriasis, dry skin, chaffed skin, diaper rash, skin rash, hives, poison ivy, skin pain, post-herpetic neuralgia, burns, wound healing, skin infections, dermatitis, atopic dermatitis, acne, impetigo, melanoma, rosacea, chapped skin, chapped lips, or skin wrinkles. In some embodiments, the dermatological compositions can be formulated as cosmetics, skin lotions, skin moisturizers, or skin creams.

In some examples, the disclosed dermatological compositions can include a bioactive agent. Examples of contemplated bioactive agents include, but are not limited to, hyaluronic acid, cholesterol, or any combination thereof.

In some examples, the disclosed dermatological composition can include an active agent. Exemplary active agents contemplated, include but are not limited to, antibiotics, antimicrobials, antifungals, antiseptics, local anesthetics, analgesics, anti-inflammatories, immunosuppressants, steroids, corticosteroids, calcineurin inhibitors, PDE4 inhibitors, salicylic acid, retinoids, antihistamines, benzoyl peroxide, and nanocrystalline silver.

Exemplary antibiotics include, but are not limited to amoxicillin, doxycycline, cephalexin, ciprofloxacin, clindamycin, metronidazole, azithromycin, sulfamethoxazole/trimethoprim, amoxicillin/clavulanate, and levofloxacin. Additional antibiotcs include Mikacin, Gentamicin, Kanamycin, Neomycin, Netilmicin, Tobramycin, Paromomycin, Streptomycin, Spectinomycin(Bs), Geldanamycin, Herbimycin, Rifaximin, Loracarbef, Ertapenem, Doripenem, Imipenem/Cilastatin, Meropenem, Cefadroxil, Cefazolin, Cephradine, Cephapirin, Cephalothin, Cefalexin, Cefaclor, Cefoxitin Cefotetan, Cefamandole, Roxithromycin, Telithromycin, Spiramycin, Fidaxomicin, Furazolidone, Nitrofurantoin(Bs), Linezolid, Posizoli, Radezolid, Torezolid, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Norfloxacin, Ofloxacin, Trovafloxacin, Minocycline, Oxytetracycline, Tetracycline, Clofazimine, Dapsone, Capreomycin, Cycloserinem Pyrazinamide, Rifampicin, Rifabutin, Rifapentine, Streptomycin, Metronidazole, and Mupirocin Exemplary antimicrobials include, but are not limited to amoxicillin, doxycycline, cephalexin, ciprofloxacin, clindamycin, metronidazole, azithromycin, sulfamethoxazole/trimethoprim, amoxicillin/clavulanate, and levofloxacin.

Exemplary antifungals include, but are not limited to, miconazole, clotrimazole, amphotericin B, ketoconazole, fluconazole, isavuconazole, itraconazole, posaconazole, voriconazole, anidulafungin, caspofungin, micafungin, and flucytosine.

Exemplary antiseptics include ethanol, sodium hypochlorite, chlorhexidine, hexachlorophene, povidone iodine, sodium hypochlorite, sodium hypochlorite, benzethonium chloride, triclosan, oxychlorosene sodium, benzalkonium chloride, and silver nitrate.

Exemplary local anesthetics include amylocaine, ambucaine, articaine, benzocaine, benzonatate, bupivacaine, butacaine, butanilicaine, chloroprocaine, cinchocaine(INN), cocaine, cyclomethycaine, dibucaine, diperodon, dimethocaine, eucaine, etidocaine, hexylcaine, fomocaine, fotocaine, hydroxyprocaine, isobucaine, levobupivacaine, lidocaine (lignocaine), mepivacaine, meprylcaine, metabutoxycaine, nitracaine, orthocaine, oxetacaine(oxethazaine), oxybuprocaine, paraethoxycaine, phenacaine, piperocaine, piridocain, pramocaine, prilocaine, primacaine, procaine, procainamide, proparacaine, propoxycaine, pyrrocaine, quinisocaine(INN), ropivacaine, trimecaine, tetracaine, tolycaine, and tropacocaine.

Exemplary analgesics include codeine, fentanyl, hydrocodone (Hysingla, Zohydro, Hydrocodone/acetaminophen (Lorcet, Lortab, Norco, Vicodin), Hydromorphone (Dilaudid, Exalgo), Meperidine (Demerol), Methadone (Dolophine, Methadose), Morphine (Kadian, MS Contin, Morphabond), Oxycodone (OxyContin, Oxaydo), Oxycodone and acetaminophen (Percocet, Roxicet), and Oxycodone and naloxone.

Exemplary anti-inflammatories include celecoxib (Celebrex), diclofenac (Cambia, Cataflam, Voltaren-XR, Zipsor, Zorvolex), diflunisal (Dolobid), etodolac (Lodine), ibuprofen (Motrin, Advil), indomethacin (Indocin), ketoprofen (Active-Ketoprofen, ketorolac, nabumetone naproxen (Aleve, Anaprox, Naprelan, Naprosyn), oxaprozin (Daypro), piroxicam (Feldene), salsalate, sulindac, and tolmetin.

Exemplary immunosuppressants include corticosteroids (e.g., prednisone (Deltasone, Orasone), budesonide (Entocort EC), prednisolone, and (Millipred)), Janus kinase inhibitors (e.g. tofacitinib (Xeljanz)), Calcineurin inhibitors, e.g., cyclosporine (Neoral, Sandimmune, SangCya), and tacrolimus (Astagraf XL, Envarsus XR, Prograf), mTOR inhibitors, e.g., sirolimus (Rapamune), and everolimus (Afinitor, Zortress), IMDH inhibitors, e.g., azathioprine (Azasan, Imuran), leflunomide (Arava), and mycophenolate (CellCept, Myfortic), biologics, e.g., abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), and monoclonal antibodies, e.g., basiliximab (Simulect), daclizumab (Zinbryta), and muromonab (Orthoclone OKT3).

Exemplary calcineurin inhibitors include astagraf XL, cyclosporine, cyclosporine ophthalmic, Elidel, Envarsus XR, Gengraf, Hecoria, Neoral, pimecrolimus, Prograf, Protopic, Restasis, Sandimmune, tacrolimus, and tacrolimus ointment.

Exemplary phosphodiesterase 4 (PDE4) inhibitors include Adibendan, Aminophylline, Aminophylline dehydrate, Amipizone, Apremilast, Arofylline, Atizoram, Befuraline, Bemarinone hydrochloride, Bemoradan, Benafentrine, Bucladesine, Buflomedil, Buquineran, CC-1088, Carbazeran, Catramilast, Cilomilast, Cilostamide, Cilostazol, Cipamfylline, Crisaborole, Daxalipram, Denbufylline, Dimabefylline, Diniprofylline, Dipyridamole, Doxofylline, Drotaverine, Dyphylline, Enoximone, Etamiphyllin, Etofylline, Filaminast, Flufylline, Fluprofylline, Furafylline, Imazodan, Imazodan hydrochloride, Inamrinone, Inamrinone lactate, Isbufylline, Lirimilast, Lisofylline, Lomifylline, Medorinone, Metescufylline, Midaxifylline, Milrinone, Milrinone lactate, Motapizone, Nanterinone, Nestifylline, Nitraquazone, Oglemilast, Oglemilast Sodium, Olprinone, Oxagrelate, Oxtriphylline, Papaverine, Papaverine hydrochloride, Papaverine sulfate, Parogrelil, Pelrinone hydrochloride, Pentifylline, Pentoxifylline, Perbufylline, Piclamilast, Pimefylline, Pimobendan, Piroximone, Prinoxodan, Proxyphylline, Pumafentrine, Quazinone, Quazodine, Revamilast, Revizinone, Roflumilast, Rolipram, Ronomilast, Saterinone, Senazodan, Siguazodan, Tetomilast, Tofimilast, Trapidil, Vesnarinone, and Zardaverine In some embodiments, the dermatological composition includes one or more active and/or bioactive agents. In some embodiments, the dermatological composition includes two active agents, for example, lidocaine and clindamycin. In another example, the dermatological composition includes an active and a bioactive agent, for example, retinol and hyaluronic acid, respectively.

In embodiments, the dermatological composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the dermatological composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes a dermatological composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the dermatological composition including a cell membrane fluidity enhancing agent (e.g., a sterol, wherein exemplary sterols include cholesterol, cholesterol derivatives, phytosterols, or any combination thereof) has a pH of about 4.5 to about 6.5. In other embodiments, the pH is about 5.5.

In some examples, the dermatological composition including a cell membrane fluidity enhancing agent (e.g., a sterol, wherein exemplary sterols include cholesterol, cholesterol derivatives, phytosterols, or any combination thereof) has an osmolarity of about 200 to about 500 mOsm/kg.

The dermatological composition should have a zero-rate viscosity that is resistant change over time and/or temperature. The terms "viscous," "viscosity," "zero-rate viscosity" and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the dermatological composition has a zero-rate viscosity of about 100 Pa-s to about 1000 kPa-s at 25° C.

In some examples, the dermatological composition including a cell membrane fluidity enhancing agent (e.g., a sterol, wherein exemplary sterols include cholesterol, cholesterol derivatives, phytosterols, or any combination thereof) has a zero-rate viscosity of about 100 Pa-s to about 1000 kPa-s at 25° C.

In some examples, the dermatological composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

As described herein, an exemplary dermatological composition comprises ceramide.

Dermatological Methods

Also provided herein are methods for providing dermatological symptom relief, treating underlying pathophysiology or infection, or prophylactically protecting a subject comprising administering to a subject any one of the compositions disclosed herein.

In some embodiments, the methods for dermatological utility comprises treating or preventing conditions including, but not limited to eczema, psoriasis, plaque psoriasis, dry skin, chaffed skin, diaper rash, skin rash, hives, poison ivy, skin pain, post-herpetic neuralgia, burns, wound protection and/or healing, skin infections, dermatitis, atopic dermatitis, acne, impetigo, melanoma, rosacea, chapped skin, chapped lips, or skin wrinkles. In other exemplary embodiments, the dermatological utility of the disclosed compositions provides that the compositions can be formulated as cosmetics, skin lotions, skin moisturizers, skin creams, or skin protectants.

Rectal Compositions

Also provided herein are rectal compositions. For example, the compositions can be used to treat or prevent hemorrhoids or anal fissures.

In some examples, the disclosed rectal compositions can include an active agent. Exemplary contemplated active agents include, but are not limited to vasoconstrictors, anti-inflammatories, steroids, local anesthetics, alpha-adrenergic receptor agonists, onabotulinumtoxin A, calcium channel inhibitors, and nitrates.

In some embodiments, the rectal composition includes one or more active agents. In some embodiments, the rectal composition includes two active agents, for example, lidocaine and hydrocortisone.

In embodiments, the rectal composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the rectal composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes a rectal composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the rectal composition including a cell membrane fluidity enhancing agent (e.g., a sterol, wherein exemplary sterols include cholesterol, cholesterol derivatives, phytosterols, or any combination thereof) has a pH of about 7 to about 8. In other embodiments, the pH is about 7.4.

In some examples, the rectal composition including a cell membrane fluidity enhancing agent (e.g., a sterol, wherein exemplary sterols include cholesterol, cholesterol derivatives, phytosterols, or any combination thereof) has an osmolarity of about 200 to about 500 mOsm/kg.

The rectal composition should have a zero-rate viscosity that is resistant change over time and/or temperature. The terms "viscous," "viscosity", "zero-rate viscosity' and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the rectal composition has a zero-rate viscosity of about 50 kPa-s to about 1000 kPa-s at 25° C.

In some examples, the rectal composition including a cell membrane fluidity enhancing agent (e.g., a sterol, wherein exemplary sterols include cholesterol, cholesterol derivatives, phytosterols, or any combination thereof) has a zero-rate viscosity of about 50 kPa-s to about 1000 kPa-s at 25° C.

In some examples, the rectal composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

Rectal Methods

Also provided herein are methods for providing rectal symptom relief or treating underlying pathophysiology or infection in a subject comprising administering to a subject any one of the compositions disclosed herein.

In some embodiments, the methods for rectal utility comprises treating conditions including, but not limited to, hemorrhoids or anal fissures.

Sunscreen Compositions

Also provided herein are sunscreen compositions. For example, the compositions can be used to treat or prevent sun damage (e.g., damage from ultraviolet radiation). Regulation of skin darkening resulting from exposure to ultraviolent light can be achieved by using the compositions described herein. Useful sunblocks include, for example, zinc oxide and titanium dioxide. Ultraviolet light is a predominant cause of skin darkening.

In embodiments, the sunscreen compositions can include an active agent. Exemplary active agents (e.g. UV-absorbing agents) in the sunscreen compositions described herein include, but are not limited to, zinc oxide, titanium dioxide, oxybenzone, avobenzone, octisalate, octocrylene, homosalate octinoxate, and para-aminobenzoic acid (e.g., PABA).

In some embodiments, the sunscreen composition includes one or more active agents capable of absorbing UV-radiation. In some embodiments, the sunscreen composition includes two active agents, for example, zinc oxide and oxybenzone.

In embodiments, the sunscreen composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the sunscreen composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes a sunscreen composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the sunscreen composition including a cell membrane fluidity enhancing agent (e.g., a sterol, wherein exemplary sterols include cholesterol, cholesterol derivatives, phytosterols, or any combination thereof) has a pH of about 4.5 to about 6.5. In other embodiments, the pH is about 5.5.

In some examples, the sunscreen composition including a cell membrane fluidity enhancing agent (e.g., a sterol, wherein exemplary sterols include cholesterol, cholesterol derivatives, phytosterols, or any combination thereof) has an osmolarity of about 200 to about 500 mOsm/kg.

The sunscreen composition should have a zero-rate viscosity that is resistant change over time and/or temperature. The terms "viscous," "viscosity", "zero-rate viscosity' and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the sunscreen composition has a zero-rate viscosity of about 100 Pa-s to about 1000 kPa-s at 25° C.

In some examples, the sunscreen composition including a cell membrane fluidity enhancing agent (e.g., a sterol, wherein exemplary sterols include cholesterol, cholesterol derivatives, phytosterols, or any combination thereof) has a zero-rate viscosity of about 100 Pa-s to about 1000 kPa-s at 25° C.

In some examples, the sunscreen composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

Sunscreen Methods

Also provided herein are methods for prophylactically protecting a subject from UV damage comprising administering to a subject any one of the compositions disclosed herein.

In some embodiments, the methods for sunscreen utility comprises treating or preventing conditions including, UV damage (e.g., sun damage) in a subject. For purposes as described herein, the compositions can be used to protect or treat against a UVA and/or UVB exposure.

Transdermal Drug Delivery Compositions

Also provided herein are transdermal drug delivery compositions. Transdermal drug delivery works well for high potency drugs (e.g. oral dosage of less than 10 mg) used to treat sub-chronic and chronic indications. Transdermal drug delivery offers a desirable route of administration, as it avoids first-pass, hepatic circulation and clearance. For example, the compositions can be used to treat or prevent pain, diabetes, neurological diseases or disorders, hormone deficiency, or nausea.

In some examples, the disclosed transdermal drug delivery compositions can include a bioactive agent. Examples of contemplated bioactive agents include, but are not limited to, serine proteases, chemical penetration enhancers, cholesterol, or any combination thereof.

In some examples, the disclosed transdermal drug delivery composition can include an active agent. Exemplary active agents contemplated, include but are not limited to, analgesics, local anesthetics, hormones, steroids, sulfonylureas, alpha-glucosidase inhibitors, thiazolidinediones, glucagon-like peptide-1 (GLP-1) agonists, dipeptidyl peptidase 4 (DDP-4) inhibitors, insulins, selective sodium-glucose transporter-2 (SGLT-2) inhibitors, antidepressants, anticonvuslants, antipsychotics, antiparkinsons, and antiemetics.

In some embodiments, the transdermal drug delivery composition includes one or more active and/or bioactive agents. In some embodiments, the transdermal drug delivery composition includes two active agents, for example, estrogen and progesterone. In another example, the transdermal drug delivery composition includes an active and a bioactive agent, for example, testosterone and serine protease, respectively.

In embodiments, the transdermal drug delivery composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the transdermal drug delivery composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes a transdermal drug delivery composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the transdermal drug delivery composition including a cell membrane fluidity enhancing agent (e.g., a sterol, wherein exemplary sterols include cholesterol, cholesterol derivatives, phytosterols, or any combination thereof) has a pH of about 4.5 to about 6.5. In other embodiments, the pH is about 5.5.

In some examples, the transdermal drug delivery composition including a cell membrane fluidity enhancing agent (e.g., a sterol, wherein exemplary sterols include cholesterol, cholesterol derivatives, phytosterols, or any combination thereof) has an osmolarity of about 200 to about 500 mOsm/kg.

The transdermal drug delivery composition should have a zero-rate viscosity that is resistant change over time and/or temperature. The terms "viscous," "viscosity", "zero-rate viscosity' and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the transdermal drug delivery composition has a zero-rate viscosity of about 100 Pa-s to about 1000 kPa-s at 25° C.

In some examples, the transdermal drug delivery composition including a cell membrane fluidity enhancing agent (e.g., a sterol, wherein exemplary sterols include cholesterol, cholesterol derivatives, phytosterols, or any combination thereof) has a zero-rate viscosity of about 100 Pa-s to about 1000 kPa-s at 25° C.

In some examples, the transdermal drug delivery composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

Transdermal Methods

Also provided herein are methods for providing a transdermal drug delivery system, the method comprising administering to a subject any one of the compositions disclosed herein.

In some embodiments, the methods for a transdermal drug delivery system comprises treating or preventing conditions including, but not limited to, pain, diabetes, neurological disorders or diseases, hormone deficiency, or nausea.

Ophthalmic Compositions

Also provided herein are ophthalmic compositions. The ophthalmic compositions described herein can be used to treat or prevent ocular surface disorders, ophthalmic diseases, ophthalmic disorders, and the like, which include, but are not limited to, dry eyes, styes, epithelial defects, retinal detachment, conjunctivitis (for example viral conjunctivitis, bacterial conjunctivitis or allergic conjunctivitis), superior limbic keratoconjunctivitis, keratoconjunctivitis sicca, neurotrophic keratopathy, Sjögren's syndrome, ocular cicatricial pemphigoid (OCP), conjunctivitis medicamentosa, corneal ulcerations and erosions, and macular degeneration. Additionally, the ophthalmic compositions can be used before or after ocular surgery, including for example, retinal surgery, penetrating keratoplasty and refractive surgery laser-assisted in situ keratomileusis (LASIK), laser epithelial keratomileusis (LASEK), or photorefractive keratectomy (PRK).

As used herein the term "ophthalmic composition" refers to a composition intended for application to the eye or its related or surrounding tissues such as, for example, the eyelid or onto the cornea. The term also includes compositions intended to therapeutically treat conditions of the eye itself or the tissues surrounding the eye. The ophthalmic composition can be applied topically or by other techniques, known to persons skilled in the art, such as injection to the eye. Examples of suitable topical administration to the eye include administration in eye drops and by spray formulations. A further suitable topical administration route is by subconjunctival injection. The compositions can also be provided to the eye periocularly or retro-orbitally.

In some examples, the disclosed ophthalmic composition can include an active agent. Exemplary active agents contemplated, include, but are not limited to, antibiotics, antimicrobials, antivirals, antiseptics, local anesthetics, antihistamines, vasoconstrictors, analgesics, anti-inflammatories, immunosuppressants, immunostimulants, immunomodulators, steroids, and corticosteroids.

In some embodiments, the ophthalmic composition includes one or more active agents. For example, the ophthalmic composition includes an vasoconstrictor and an antihistamine, e.g., naphazoline and pheniramine.

In embodiments, the ophthalmic composition includes an active agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the ophthalmic composition includes a bioactive agent from about 0.0001 percent by weight to about 90 percent by weight of the composition, from about 0.0001 percent by weight to about 1 percent by weight, from about 0.0001 percent by weight to about 10 percent by weight, from about 0.0001 percent by weight to about 20 percent by weight, from about 0.0001 percent by weight to about 30 percent by weight, from about 0.0001 percent by weight to about 40 percent by weight, from about 0.0001 percent by weight to about 50 percent by weight, from about 0.0001 percent by weight to about 60 percent by weight, from about 0.0001 percent by weight to about 70 percent by weight, from about 0.0001 percent by weight to about 80 percent by weight, from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the present disclosure includes an ophthalmic composition including a cell membrane fluidity enhancing agent (e.g., a sterol, wherein exemplary sterols include cholesterol, cholesterol derivatives, phytosterols, or any combination thereof) and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium, sorbic acid, benzoic acid, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, potassium sorbate, sodium proprionate, and sodium perborate, or any combination(s) thereof.

In embodiments the preservatives may be used in any suitable amounts. For example, the preservative may be used in an amount about 0.001% by weight-1.0% by weight based on the total weight of composition.

In embodiments, the ophthalmic composition including a cell membrane fluidity enhancing agent (e.g., a sterol, wherein exemplary sterols include cholesterol, cholesterol derivatives, phytosterols, or any combination thereof) has a pH of about 7 to about 7.4 (e.g. neutral pH, or physiological pH). In other embodiments, the pH is about 7.

In some examples, the ophthalmic composition including a cell membrane fluidity enhancing agent (e.g., a sterol, wherein exemplary sterols include cholesterol, cholesterol derivatives, phytosterols, or any combination thereof) has an osmolarity of about 200 to about 500 mOsm/kg.

The ophthalmic composition should have a zero-rate viscosity that is resistant change over time and/or temperature. The terms "viscous," "viscosity", "zero-rate viscosity" and the like refer herein, in the usual and customary sense, to a measure of the resistance of a material to deformation (e.g., liquid behavior) upon application of a force (e.g., shear stress or tensile stress). The viscosity of the emulsions can also depend on the temperature, along with several other effects, such as shear rate, average droplet size, and droplet size distribution. As described herein, the viscosity may typically mean that the ophthalmic composition has a zero-rate viscosity of about 100 Pa-s to about 1000 kPa-s at 25° C.

In some examples, the ophthalmic composition including a cell membrane fluidity enhancing agent (e.g., a sterol, wherein exemplary sterols include cholesterol, cholesterol derivatives, phytosterols, or any combination thereof) has a zero-rate viscosity of about 100 Pa-s to about 1000 kPa-s at 25° C.

In some examples, the ophthalmic composition including a cell membrane fluidity enhancing agent (e.g., a sterol, wherein exemplary sterols include cholesterol, cholesterol derivatives, phytosterols, or any combination thereof) has rheological properties that have negligible variation with temperature between 25° C. and 37° C.

Ophthalmic Methods

Also provided herein are methods for providing ophthalmic symptom relief, treating underlying pathophysiology or infection, or prophylactically protecting a subject comprising administering to a subject any one of the compositions disclosed herein. In some embodiments, the methods for ophthalmic utility comprises treating or preventing conditions including, but not limited to ocular surface disorders, ophthalmic diseases, ophthalmic disorders, and the like, which include, but are not limited to, dry eyes, styes, epithelial defects, retinal detachment, conjunctivitis (for example viral conjunctivitis, bacterial conjunctivitis or allergic conjunctivitis), superior limbic keratoconjunctivitis, keratoconjunctivitis sicca, neurotrophic keratopathy, Sjögren's syndrome, ocular cicatricial pemphigoid (OCP), conjunctivitis medicamentosa, corneal ulcerations and erosions, and macular degeneration. Additionally, the ophthalmic compositions can be used before or after ocular surgery, including for example, retinal surgery, penetrating keratoplasty and refractive surgery laser-assisted in situ keratomileusis (LASIK), laser epithelial keratomileusis (LASEK), or photorefractive keratectomy (PRK). In other exemplary embodiments, the ophthalmic utility of the disclosed compositions provides that the compositions can be formulated as a solution, a suspension, a semi-solid, an emulsion, semi-liquid, an ointment, a cream, or a controlled-release/sustained-release vehicle. For example, the composition may be in the form of a contact lens solution, eye drop, eye ointment, and the like.

In embodiments, the method of treating ophthalmic conditions includes treating dry eye associated with or resulting from treating inflammation of the surface of the eye, the lacrimal gland, or the conjunctiva; dry eye associated with any disease process that alters the components of the tears;

dry eye associated with an increase in the surface of the eye, as in thyroid disease when the eye protrudes forward; and/or dry eye associated with a cosmetic surgery, for example, if the eyelids are opened too widely during surgery.

In embodiments, the method of treating ophthalmic conditions includes ameliorating a symptoms, including: stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses; decreased tolerance of reading, working on the computer, or any activity that requires sustained visual attention; and/or eye fatigue.

Additional Applications

The compositions, as described herein can be also formulated for a variety of industrial applications, including but not limited to for providing lubrication, protection, or moisturization of the surfaces to which it is applied.

For example, the compositions of the present invention have many applications in such areas as auto and motor sports applications; boating applications; farming applications; garage/workshop applications; hobby and crafts applications; and home and garden applications. For example, the composition can be used to provide a protective coating on metal objects to prevent rust from forming; to provide lubrication to contacting metal parts; to clean and lubricate moving parts; to lubricate and penetrate stuck objects; to clean and lubricate tools, saws, and blades; to restore or polish a surface (after physicochemical change to the surface). Exemplary surfaces include wood, porcelain, enamel, tile, stainless steel, fiberglass, chrome, and rubber.

Kits

Also provided herein are kits for a composition for symptom relief, treating underlying pathophysiology or infection of the anatomy associated with the condition, or prophylactically protecting the anatomy in a subject. In embodiments, the kit comprises a stable water-in-silicone emulsion and a cell membrane fluidity enhancing agent. In other embodiments, the kit also includes an emulsifier, a fatty acid, a preservative, and at least one of, a bioactive agent, a pH buffering system, a viscosity enhancing agent, an antioxidant, a tocopherol, a ceramide, or an active agent, and instructions for producing the composition. The instructions may describe the steps and reagents for producing the composition by emulsification. Such steps and reagents may be in accordance with those that the present application discloses for emulsification.

In embodiments, provided herein are kits for producing a vulvovaginal composition for providing vulvovaginal symptom relief, treating underlying pathophysiology or infection of the vulvovaginal anatomy, or prophylactically protecting the vulvovaginal anatomy in a subject; the kit comprising, consisting of, or consisting essentially of a stable water-in-silicone emulsion, an emulsifier, a cell membrane fluidity enhancing agent, a fatty acid, a preservative, and at least one of, a bioactive agent, a pH buffering system, a viscosity enhancing agent, an antioxidant, a tocopherol, and an active agent, and instructions for producing the vulvovaginal composition. The instructions may describe the steps and reagents for producing the vulvovaginal composition by emulsification. Such steps and reagents may be in accordance with those that the present application discloses for emulsification.

Also provided herein are dermatological kits comprising the compositions described herein. The dermatological kits provided herein are for treating or preventing conditions including, but not limited to eczema, psoriasis, plaque psoriasis, dry skin, chaffed skin, diaper rash, skin rash, hives, poison ivy, skin pain, post-herpetic neuralgia, burns, wound healing, skin infections, dermatitis, atopic dermatitis, acne, impetigo, melanoma, rosacea, chapped skin, chapped lips, or skin wrinkles. In other exemplary embodiments, the dermatological kits of the disclosed compositions provides that the compositions of the kits can be formulated as cosmetics, skin lotions, skin moisturizers, skin creams, or skin protectants.

In other examples, also provided herein are rectal kits comprising the compositions described herein. The rectal kits provided herein are for treating or preventing conditions including, but not limited to hemorrhoids or anal fissures.

In other examples, also provided herein are sunscreen kits comprising the compositions described herein. The sunscreen kits provided herein are for treating or preventing conditions including, but not limited to, UV damage (e.g., sun damage).

In other examples, also provided herein are transdermal drug delivery system kits comprising the compositions described herein. The transdermal drug delivery system kits provided herein are for treating or preventing conditions including, but not limited to, pain, diabetes, neurological disorders or diseases, hormone deficiency, or nausea.

In other examples, also provided herein are ophthalmic kits comprising the compositions described herein. The ophthalmic kits provided herein are for treating or preventing conditions, including, but not limited to, ocular surface disorders, ophthalmic diseases, ophthalmic disorders, and the like.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Vulvovaginal Cream Produced by Water-in-Silicone (W/O) Emulsification A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 1% by weight Span 80, 2% by weight Tween 80, 1% by weight cholesterol, 0.2% by weight stearic acid, 0.2% by weight oleic acid, 0.2% by weight linoleic acid, 1% by weight tocopheryl acetate, and 0.1% by weight benzoic acid, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, and 0.1% by weight benzoic acid, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Example 2: Vulvovaginal Cream with Active Agent Produced by Water-in-Silicone (W/O) Emulsification Vulvovaginal Cream with 2% Miconazole Produced by Water-in-Silicone (W/O) Emulsification.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, 0.1% by weight benzoic acid, and 3% by weight miconazole, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Vulvovaginal Cream with 1% Clotrimazole Produced by Water-in-Silicone (W/O) Emulsification.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, 0.1% by weight benzoic acid, and 1.5% by weight clotrimazole is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Vulvovaginal Cream with 1% Metronidazole Produced by Water-in-Silicone (W/O) Emulsification.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, 0.1% by weight potassium sorbate, and 1.5% by weight metronidazole, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, 0.1% by weight benzoic acid, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Vulvovaginal Cream 4% Nonoxynol-9 Produced by Water-in-Silicone (W/O) Emulsification.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, 0.1% by weight benzoic acid, and 6% by weight nonoxynol-9, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Vulvovaginal Cream with 0.1% Estradiol Produced by Water-in-Silicone (W/O) Emulsification.

A W/O emulsified cream is fabricated with a high shear mixing method utilizing a rotor-stator homogenizer. An aqueous dispersant phase comprising a lactic acid buffering system (lactic acid/sodium lactate, pH 3.8, 250 mOsm/kg), 0.5% by weight glycogen, 0.1% by weight sodium ascorbate, and 0.1% by weight potassium sorbate, is prepared by dissolving the components in deionized water. A silicone continuous phase comprising 2% by weight PEG/PPG-18/18 dimethicone, 1% by weight octyldodecanol, 1% by weight cholesterol, 0.2% by weight stearic acid, 0.2% by weight oleic acid, 0.2% by weight linoleic acid, 1% by weight tocopheryl acetate, 0.1% by weight benzoic acid, and 0.15% by weight estradiol, is prepared by dissolving these components in dimethicone. The resulting aqueous dispersant phase (250 mL) is added to the resulting silicone continuous phase (500 mL) under constant high shear mixing using a rotor-stator homogenizer. The resulting stable microemulsion is homogenized for 30 minutes to yield a stable, water-in-silicone emulsified cream.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Example 3: Vulvovaginal Cream Prepared by Water-in-Silicone (W/O) Emulsification Methods A water-in-silicone emulsified cream was fabricated with a high shear mixing method utilizing a Silverson rotor-stator homogenizer. Briefly, an aqueous dispersant phase comprising 36.4% by weight lactic acid buffering system (100 mM lactic acid/sodium lactate buffer, pH 3.8, 300 mOsm/kg), and 0.1% by weight glycogen, was prepared by dissolving the components in deionized water with mixing at 80° C. (deionized water was compensated to account for evaporative loss during heating). A silicone continuous phase comprising 13% by weight 2-octyldodecanol, 0.25% by weight Span 60, 2% by weight cholesterol, 0.2% by weight stearic acid, and 0.1% tocopheryl acetate was prepared by dissolving these components in a mixture of 35.65% by weight dimethicone and 12.3% by weight dimethicone/dimethiconol with mixing at 80° C. The resulting aqueous dispersant phase (80° C.) was added to the resulting silicone continuous phase (80° C.) under constant high shear mixing using a Silverson rotor-stator homogenizer operating at 6500 RPM for 10 minutes. The shear rate of emulsification was then increased to 8000 RPM for 5 minutes to yield a stable, water-in-silicone emulsified cream. The stable microemulsion was then transferred to an overhead stirrer to cool by ambient equilibration to room temperature and yield a stable, solidified water-in-silicone emulsified cream. All weight percent of constituents represent percent of the total composition.

Rheology: Flow Stress Sweep Protocol

A flow stress sweep protocol was performed on a TA Instruments Discovery HR-3 stress controlled rheometer with a 20 mm parallel plate geometry and a 1000 μm gap at 25° C. and 37° C. To execute the protocol, the instrument parameters were set as follows:

Step 1) Conditioning—Options
 Mode disabled
 Purge gas only (no active cooling): off mode disabled
Step 2) Flow Sweep
 Temperature 25° C. inherit set point: Off
 Soak time 60.0 sec wait for temperature: On
 Logarithmic sweep
 Stress: 0.1-500 Pa
 Points per decade: 5
 Steady-state sensing: On (max equilibration time 60.0 sec)
 Saple period: 10.0 sec
 % tolerance: 5.0
 Consecutive within: 3
 Scaled time average: Off Rheology: Oscillatory Frequency and Amplitude Sweep Protocol An oscillatory frequency and amplitude sweep protocol was performed on a TA Instruments Discovery HR-3 stress controlled rheometer with a 20 mm parallel plate geometry and a 1000 μm gap at 25° C. and 37° C. To execute the protocol, the instrument parameters were set as follows:

Step 1) Oscillation—Frequency
 Temperature inherit set point: On
 Soak time 0.0 sec wait for temperature: Off
 Strain %: 1%
 Logarithmic sweep
 Frequency: 0.1-30 Hz
 Points per decade: 5
Step 2) Oscillation—Frequency
 Temperature inherit set point: On
 Soak time 0.0 sec wait for temperature: Off
 Strain %: 1%
 Logarithmic sweep
 Frequency: 30-0.1 Hz
 Points per decade: 5
Step 3) Oscillation—Amplitude
 Temperature inherit set point: On
 Angular Frequency: 10 rad/s
 Logarithmic sweep
 Strain %: 0.1-100%
 Points per decade: 10

Rheology: Oscillatory Temperature Sweep Protocol

An oscillatory temperature sweep protocol was performed on a TA Instruments Discovery HR-3 stress controlled rheometer with a 20 mm parallel plate geometry and a 1000 μm gap from 20° C. to 40° C. with a stress of 5 Pa and frequency of 10 rad/s. To execute the protocol, the instrument parameters were set as follows:

Step 1) Conditioning—Sample
 Temperature 20° C. inherit set point: Off
 Soak time 600.0 sec wait for temperature: On
 Wait for axial force: Off
 Perform preshear: Off
 Perform equilibration: Off
Step 2) Oscillation—Temperature Ramp
 Start temperature: 20° C.
 Soak time 60.0 sec wait for temperature: On
 End temperature: 40° C.
 Soak time after ramp: 0.0 sec
 Ramp rate: 0.5° C./min
 Sampling interval: 10 s/pt
 Stress: 5 Pa
 Single point
 Angular frequency: 10 rad/s Rheology: Results and Discussion

TABLE 1

Water-in-silicone emulsified cream formulation matrix

| Formulation # | DiM | DiM/DiM-ol | 2-octyl dodecanol | Chol | Span 60 | SA | TA | Glyc | LA | Stable Emulsion? |
|---|---|---|---|---|---|---|---|---|---|---|
| 1 | 60.0 | — | 5.0 | 2.0 | 0.5 | — | — | — | 32.5 | N |
| 2 | 50.0 | 10.0 | 5.0 | 2.0 | 0.5 | — | — | — | 32.5 | N |
| 3 | 50.0 | 10.0 | 5.0 | 4.0 | 0.5 | — | — | — | 30.5 | N |
| 4 | 50.0 | 10.0 | 5.0 | 2.0 | 1.0 | — | — | — | 32.0 | N |
| 5 | 45.0 | 10.0 | 10.0 | 2.0 | 0.5 | — | — | — | 32.5 | N |
| 6 | 40.0 | 15.0 | 10.0 | 2.0 | 0.5 | — | — | — | 32.5 | N |
| 7 | 40.0 | 15.0 | 10.0 | 2.0 | 0.25 | — | — | — | 32.75 | N |

TABLE 1-continued

Water-in-silicone emulsified cream formulation matrix

| Formulation # | DiM | DiM/ DiM-ol | 2-octyl dodecanol | Chol | Span 60 | SA | TA | Glyc | LA | Stable Emulsion? |
|---|---|---|---|---|---|---|---|---|---|---|
| 8 | 40.0 | 15.0 | 13.0 | 2.0 | 0.25 | — | — | — | 29.75 | Initially Y |
| 9 | 35.0 | 12.5 | 13.0 | 2.0 | 0.25 | — | — | — | 36.25 | Y |
| 10 | 35.75 | 12.3 | 13.0 | 2.0 | 0.25 | 0.2 | — | 0.1 | 36.4 | Y |
| 11 | 35.65 | 12.3 | 13.0 | 2.0 | 0.25 | 0.2 | 0.1 | 0.1 | 36.4 | Y |
| 12 | 12.3 | 36.65 | 13.0 | 2.0 | 0.25 | 0.2 | 0.1 | 0.1 | 36.4 | N |
| 13 | 37.95 | 10.00 | 13.00 | 2.0 | 0.25 | 0.2 | 0.1 | 0.1 | 36.4 | Y |
| 14 | 37.95 | 10.00 | 15.00 | 0.0 | 0.25 | 0.2 | 0.1 | 0.1 | 36.4 | N |

Figure 3C:
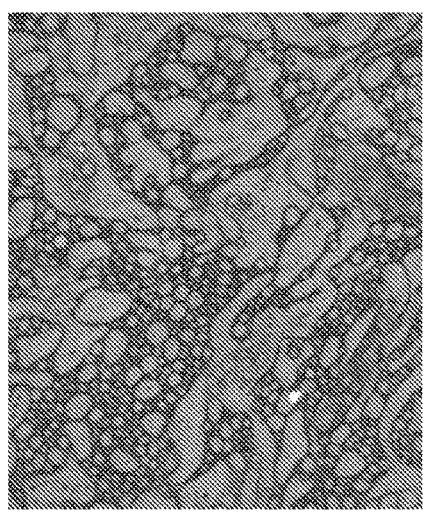
FIG. 3A-3C illustrates optical imaging of Formulation #8.
Figure 3B:
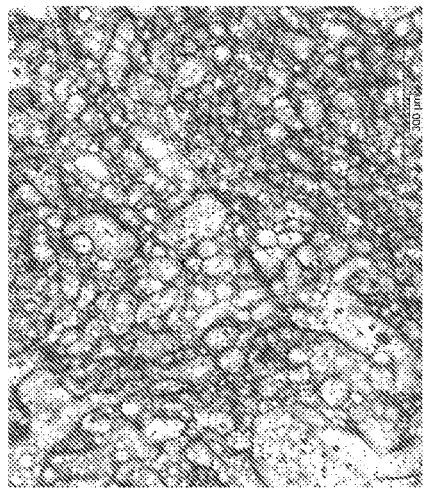
Figure 3A:
Figure 4C:
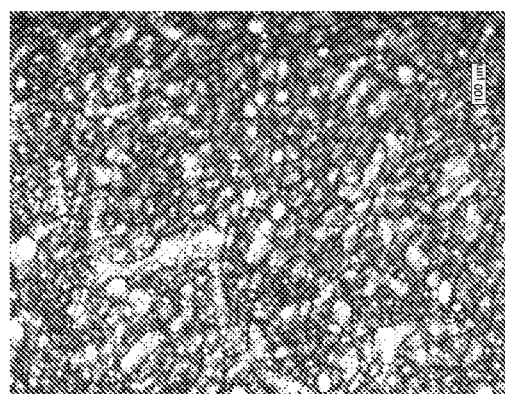
FIG. 4A-4C illustrates optical imaging of Formulation #9.
Figure 4B:
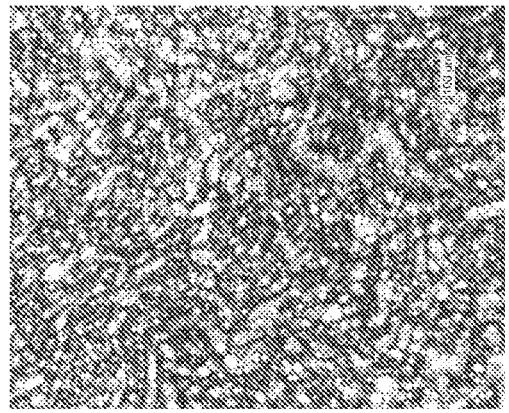
Figure 4A:
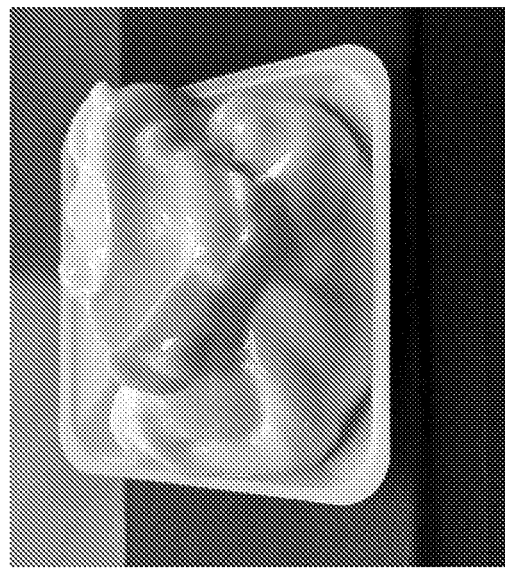
Figure 6A:
FIG. 6A-6E illustrates optical imaging of Formulations #13 and #14.
Figure 6B:
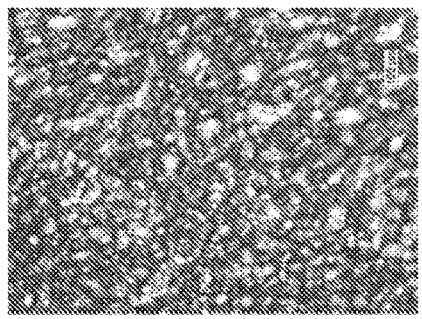
Figure 6C:
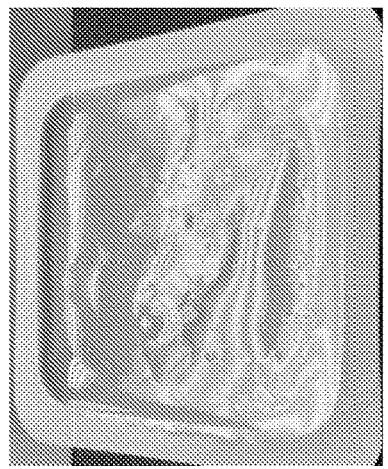
Figure 6D:
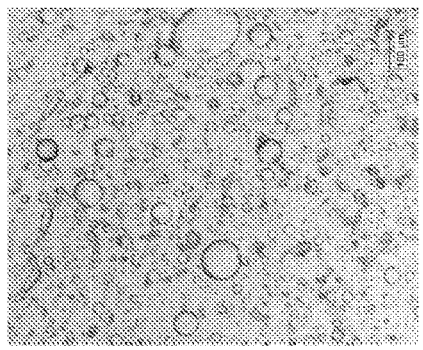
Figure 6E:
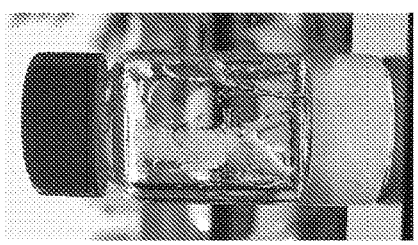
Figure 7A:
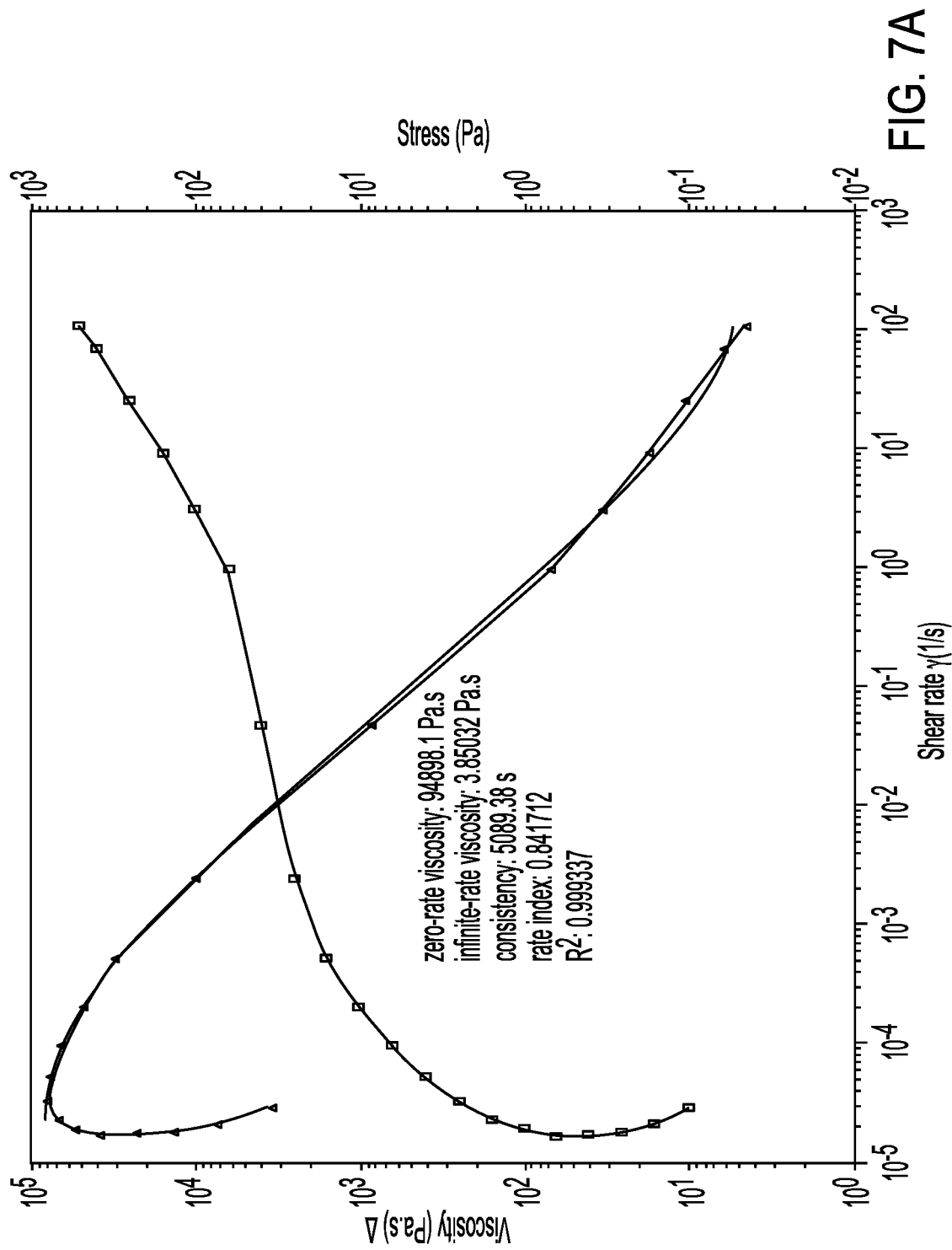
FIG. 7A-7D illustrates graphs of flow stress sweep analysis of Formulation #9.
Figure 7B:
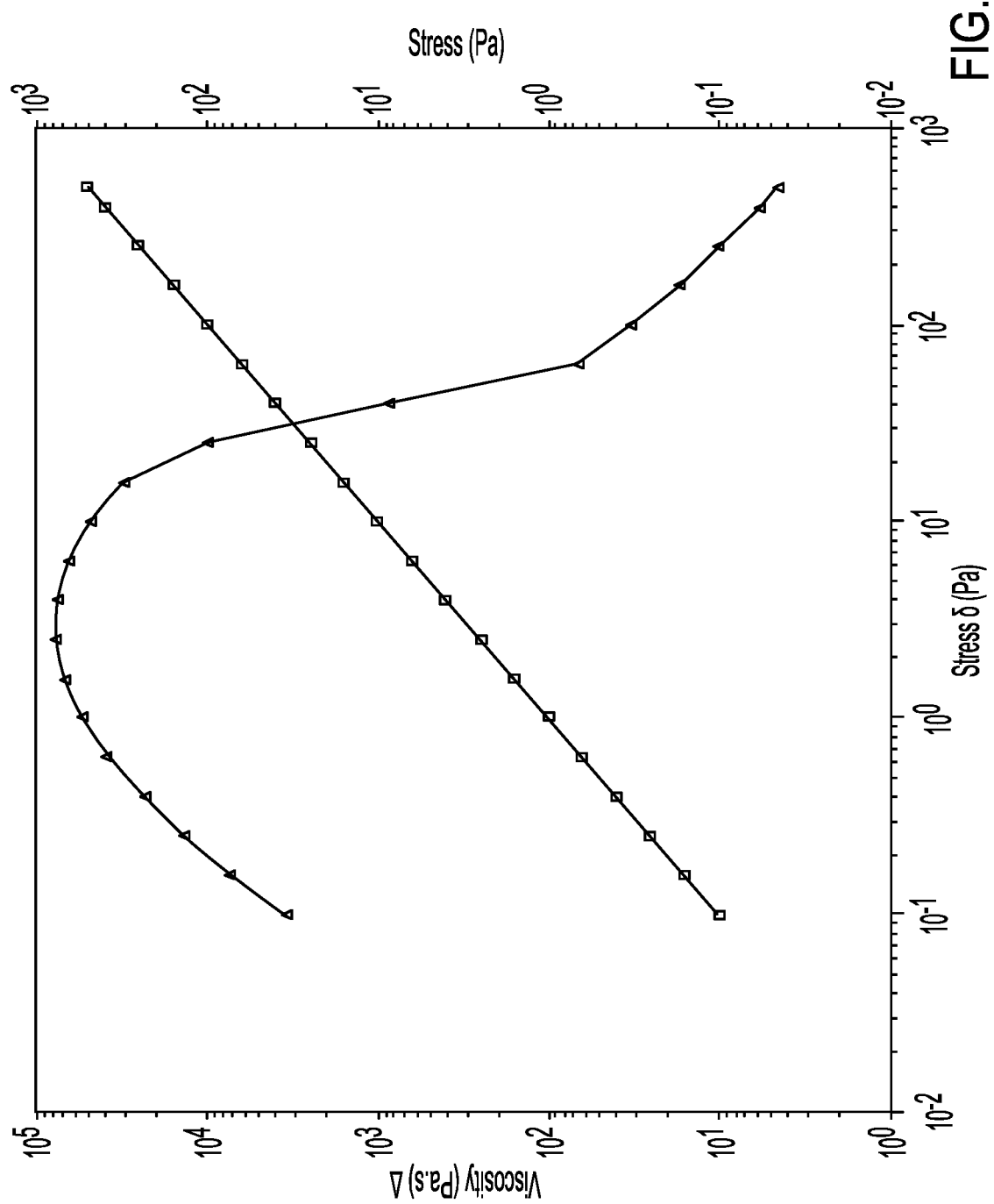
Figure 7C:
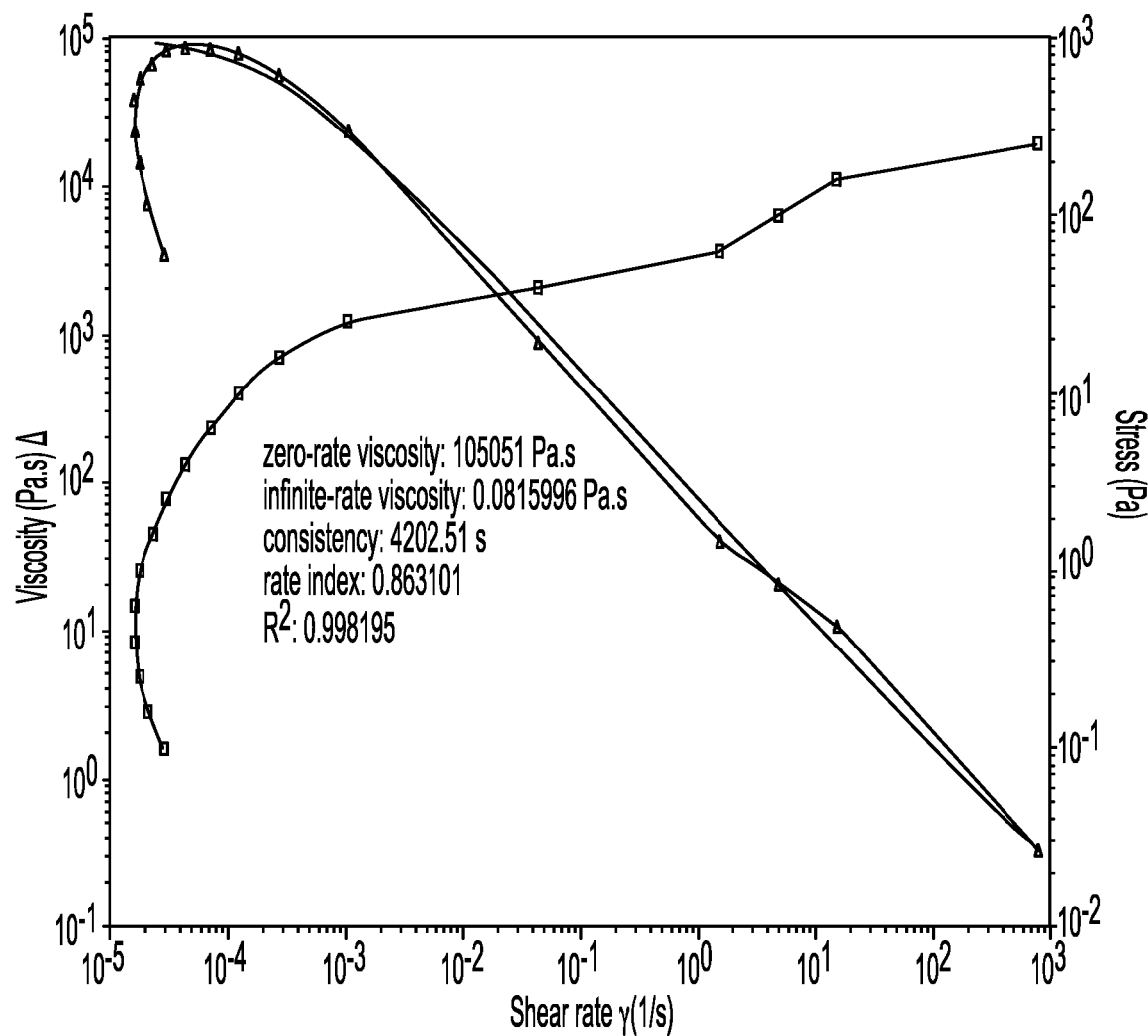
Figure 7D:
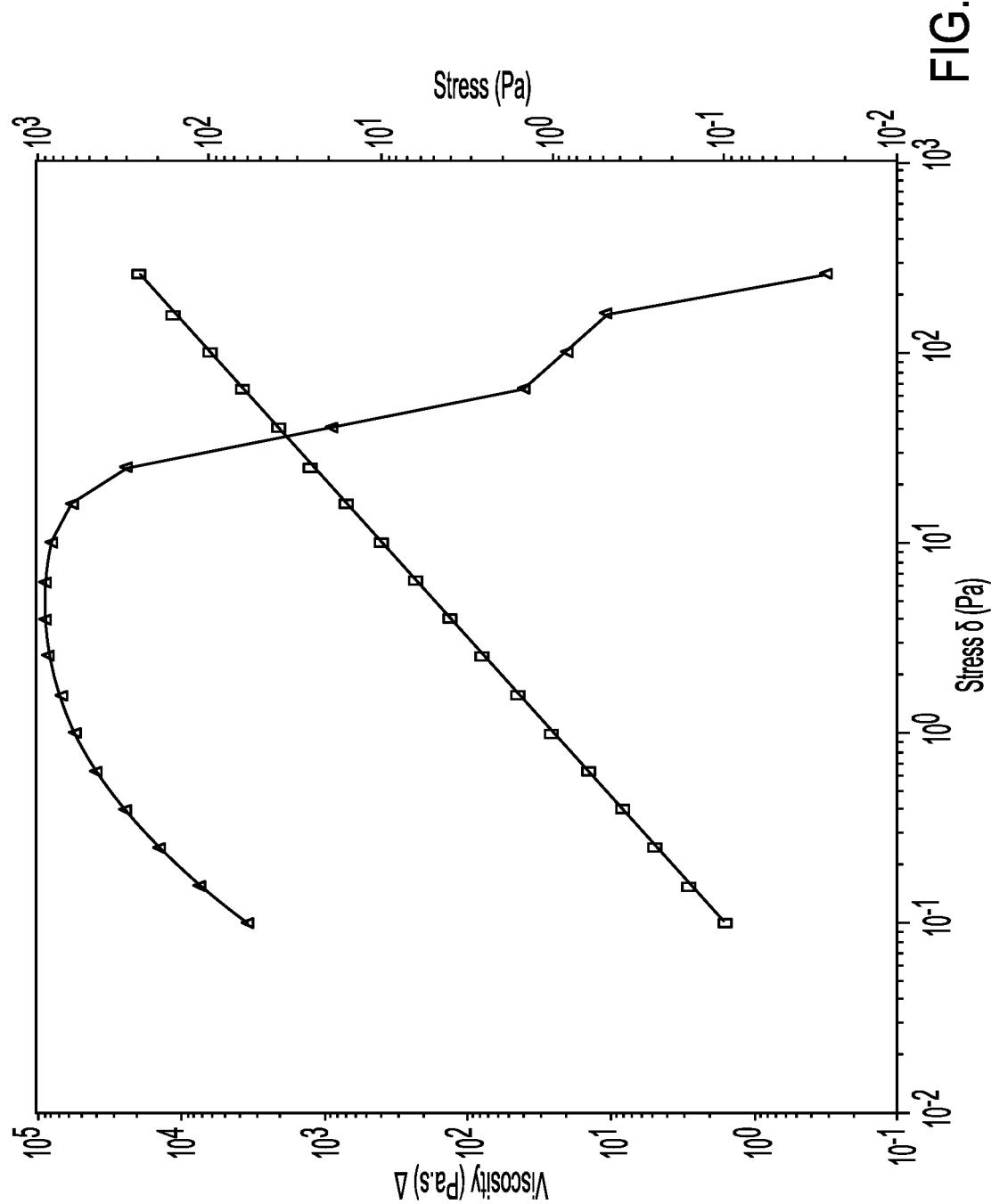

Abbreviations:
DiM = Dimethicone,
DiM/DiM-ol = Dimethicone/Dimethiconol,
Chol = Cholesterol,
SA = stearic acid,
TA = tocopheryl acetate,
Glyc = Glycogen,
LA = Lactic acid/Na lactate aqueous buffer Formulations were generated according to Table 1 and analyzed through both macroscopic and microscopic optical imaging to determine stability. Formulation #1 yielded a moderately viscous white cream in the absence of stable, classical emulsion. Phase separation initiated on day 10 and was observed to progressively increase. Formulation #2 yielded a higher viscosity white cream in the absence of stable, classical emulsion. The higher viscosity was attributed to the incorporation of dimethiconol. Phase separation initiated on day 10 and was observed to progressively increase. Formulation #3 yielded a viscous white cream in the absence of stable, classical emulsion. Phase separation was initially observed on day 1 indicating the existence of an upper limit to cholesterol incorporation. Formulation #4 failed to yield both a viscous white cream and a stable, classical emulsion. Phase separation was observed immediately following emulsification indicating the existence of an upper limit to Span 60 incorporation. This phenomenon was likely correlated to the concentration of Span 60 being above the critical micelle concentration (CMC) of Span 60 in the mixed silicone. Formulation #5 yielded a viscous white cream in the absence of stable, classical emulsion. Phase separation initiated on day 14 and was observed to progressively increase. This phenomenon was likely correlated to the increased 2-octyldodecanol creating a better interface with the Span 60 and cholesterol to better stabilize the water droplets at the water-silicone interface. Formulation #6 yielded a viscous white cream in the absence of stable, classical emulsion. Phase separation initiated on day 4 and was observed to progressively increase. This phenomenon indicated that trying to physically confer stability to the emulsion through increasing of the waxy, dimethiconol component is futile, thus, the emulsion stability is governed predominantly by physiochemical and thermodynamic parameters. Formulation #7 yielded a viscous white cream in the absence of stable, classical emulsion. Phase separation initiated on day 5 and was observed to progressively increase. This phenomenon indicated the utility of decreasing the Span 60 concentration. Formulation #8 yielded a viscous white cream in the presence of an emulsion more consistent with a stable, classical emulsion (FIG. 3A-3C). Weeping of the silicone phase was observed on day 6, though the emulsion was observed to maintain moderate stable integrity. Phase separation initiated on day 15 and was observed to progressively increase. This phenomenon further supports the hypothesis that a specific balance of the emulsifiers in essential to conferring emulsion stability. Further, the weeping of the oil phase indicated that the ratio of water to silicone should be altered to incorporate more aqueous dispersant phase. Formulation #9 yielded a viscous white cream in the presence of a stable, classical emulsion (FIG. 4A-4C). This cream has shown no signs of phase separation or instability, confirming the importance of the water to silicone ratio for emulsion stability. Formulation #10 (FIG. 5A-5C) and Formulation #11 also yielded a viscous white cream in the presence of a stable, classical emulsion. These creams have shown no signs of phase separation or instability. Formulation #12 yielded a viscous white cream in the absence of stable, classical emulsion. This phenomenon demonstrated the importance of controlling the silicone phase constituents. Formulation #13 also yielded a viscous white cream in the presence of a stable, classical emulsion. Removal of cholesterol from Formulation #13 to create Formulation #14, yielded complete phase separation and a lack of emulsion formation (FIG. 6A-6E). This phenomenon demonstrated the importance of cholesterol as an emulsifier and interfacial stabilizer.

The mechanical properties of select formulations were examined by rheometry and the results are summarized in Table 2 below.

TABLE 2

Comparison of the rheological properties with predicate vulvovaginal creams

| | Zero Rate Viscosity (kPa-s) | | Frequency Sweep | Amplitude Sweep Comparison (Crossover) | | Amplitude Sweep Comparison (Strain) | |
|---|---|---|---|---|---|---|---|
| Formulation | 25° C. | 37° C. | Comparison | 25° C. | 37° C. | 25° C. | 37° C. |
| Monistat 7 | 45 | 95 | Some widening | 1800 Pa | 1.9 Pa | 0.5% | 1.3% |
| Vagisil | 329 | 142 | Some widening | 386.8 Pa | 326.2 Pa | 29.2% | 30.4% |
| #9 | 95 | 105 | No widening | 323.6 Pa | 435.6 Pa | 10.4% | 11.3% |

TABLE 2-continued

Comparison of the rheological properties with predicate vulvovaginal creams

| Formulation | Zero Rate Viscosity (kPa-s) | | Frequency Sweep Comparison | Amplitude Sweep Comparison (Crossover) | | Amplitude Sweep Comparison (Strain) | |
| --- | --- | --- | --- | --- | --- | --- | --- |
| | 25° C. | 37° C. | | 25° C. | 37° C. | 25° C. | 37° C. |
| #10 | 346.4 | 198.6 | No widening | 336.1 Pa | 248.3 Pa | 12.1% | 11.9% |
| #11 | 166.8 | 261.1 | No widening | 288.2 Pa | 374.8 Pa | 7.45% | 8.56% |
| #13 | 315.8 | 143.2 | No widening | 384.2 Pa | 292.3 Pa | 12.4% | 12.5% |

Figure 8A:
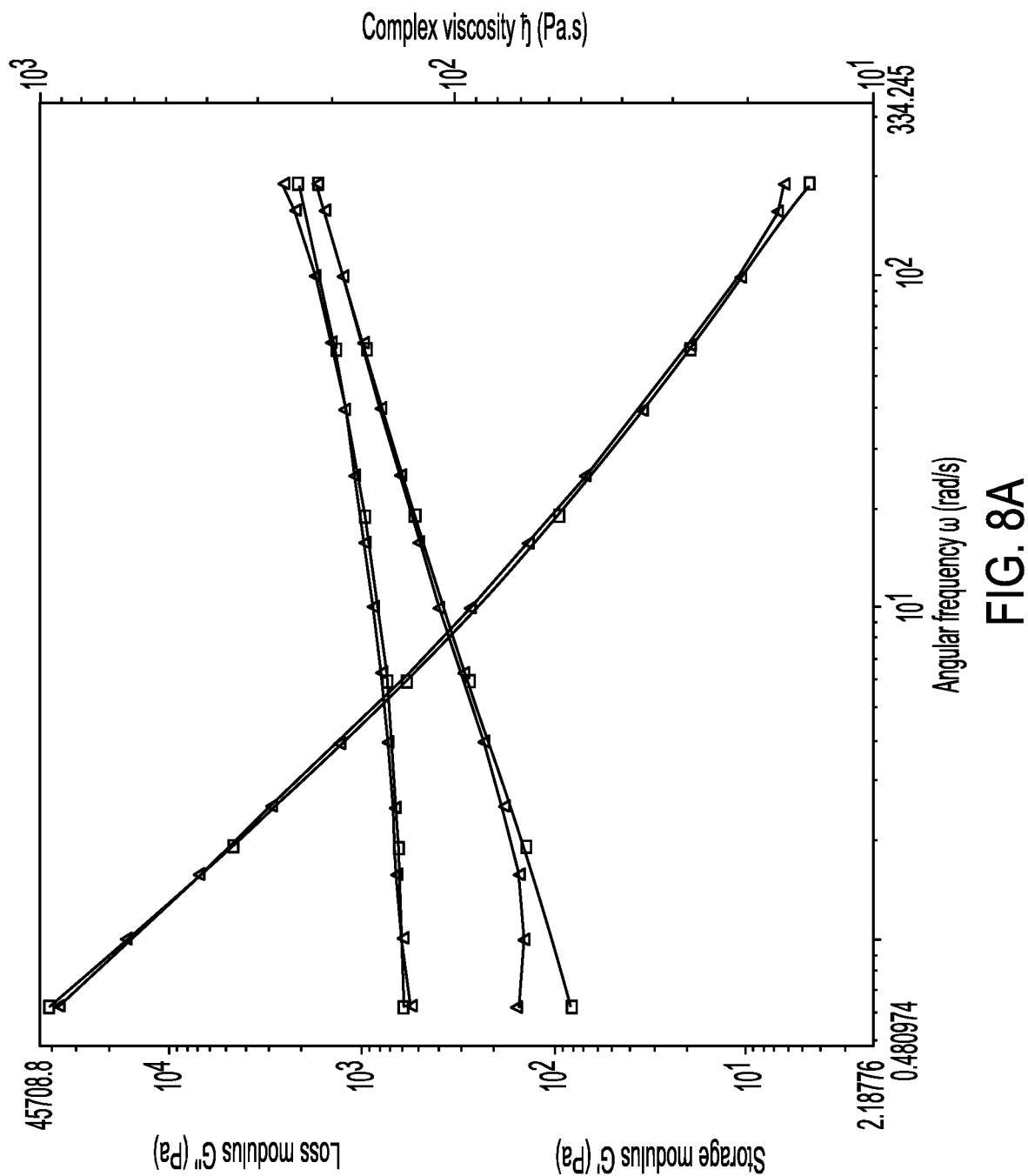
FIG. 8A-8B illustrates an oscillatory amplitude sweep of Formulation #9.
Figure 8B:
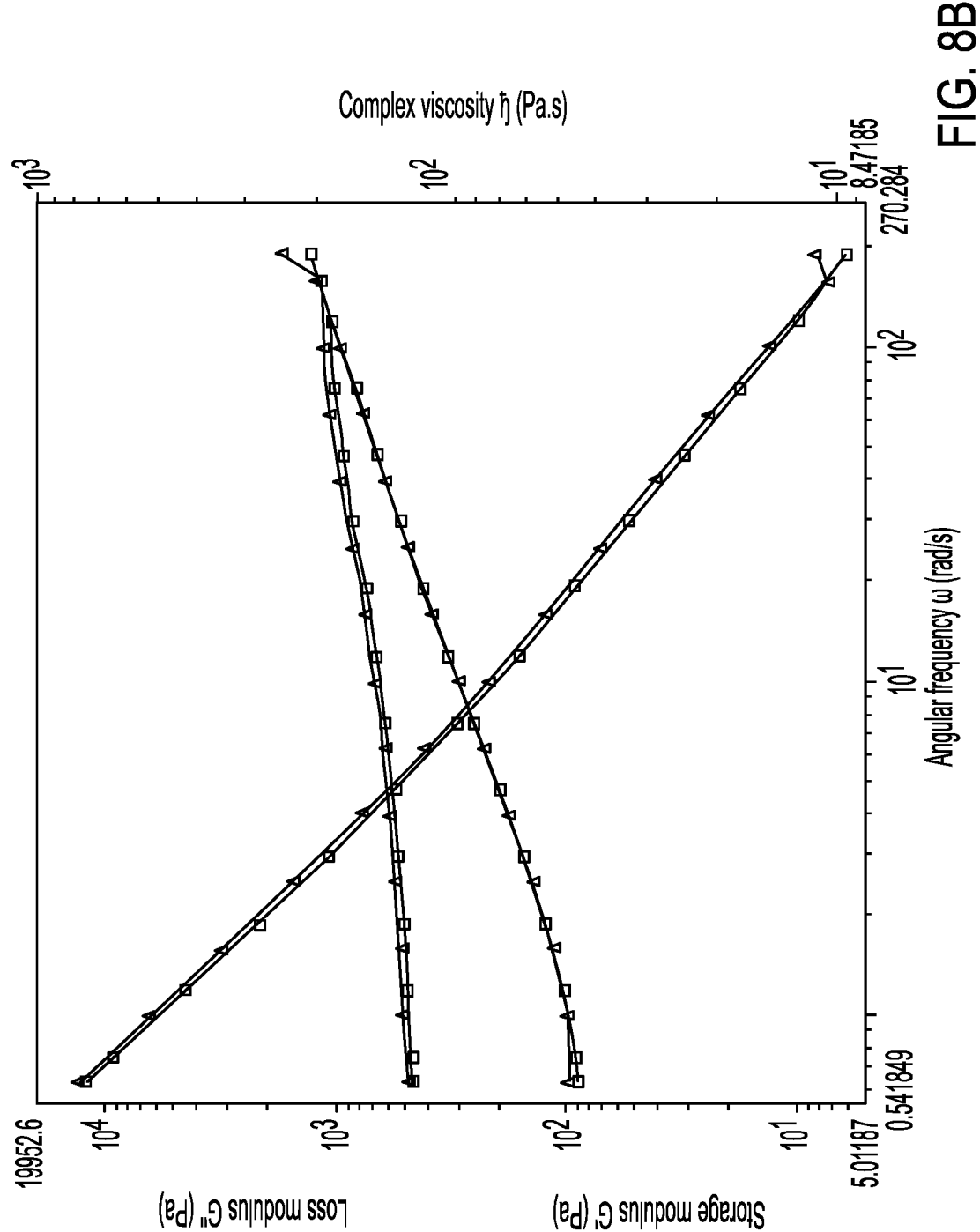
Figure 9A:
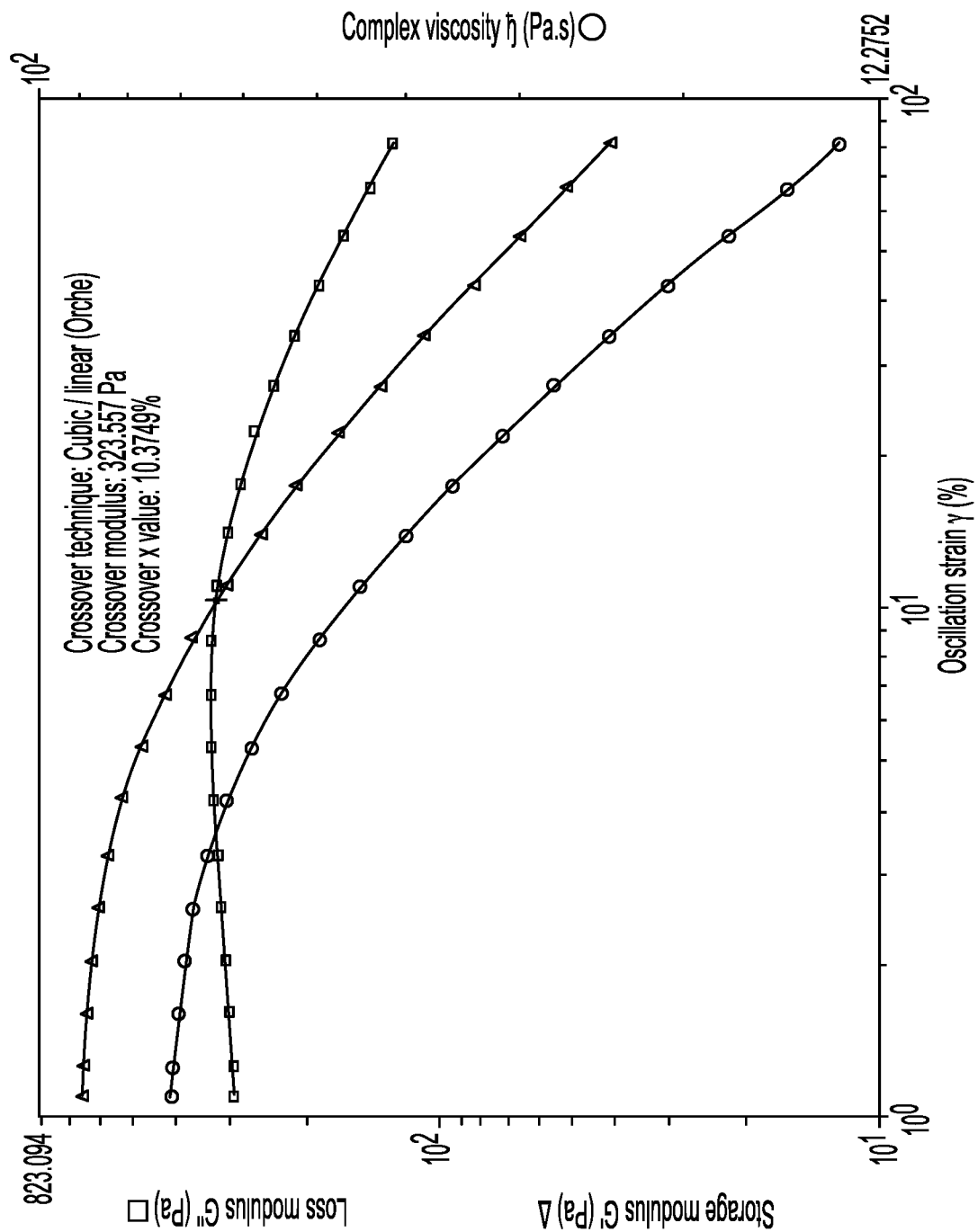
FIG. 9A-9B illustrates an oscillatory frequency sweep of Formulation #9.
Figure 9B:
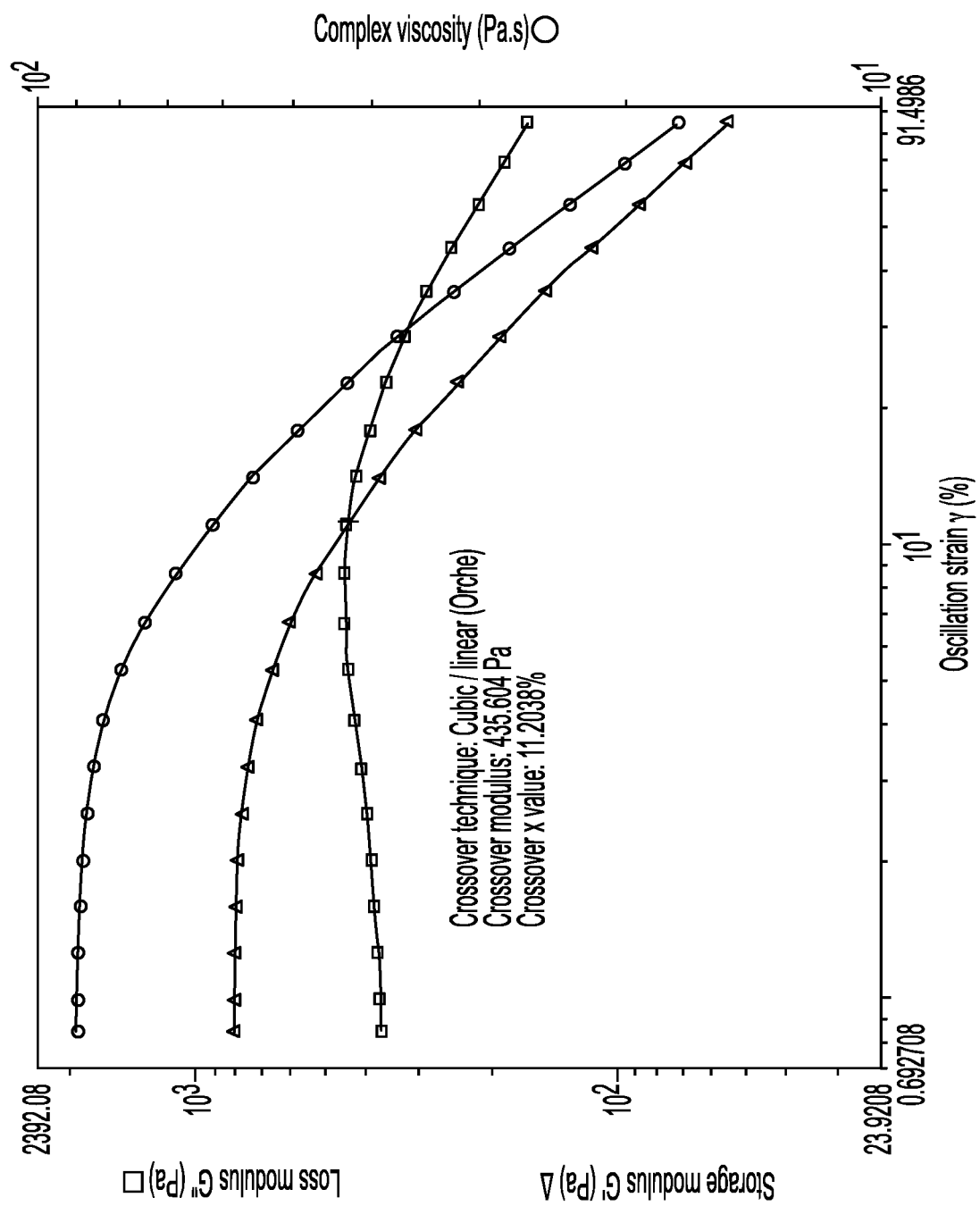
Figure 10:
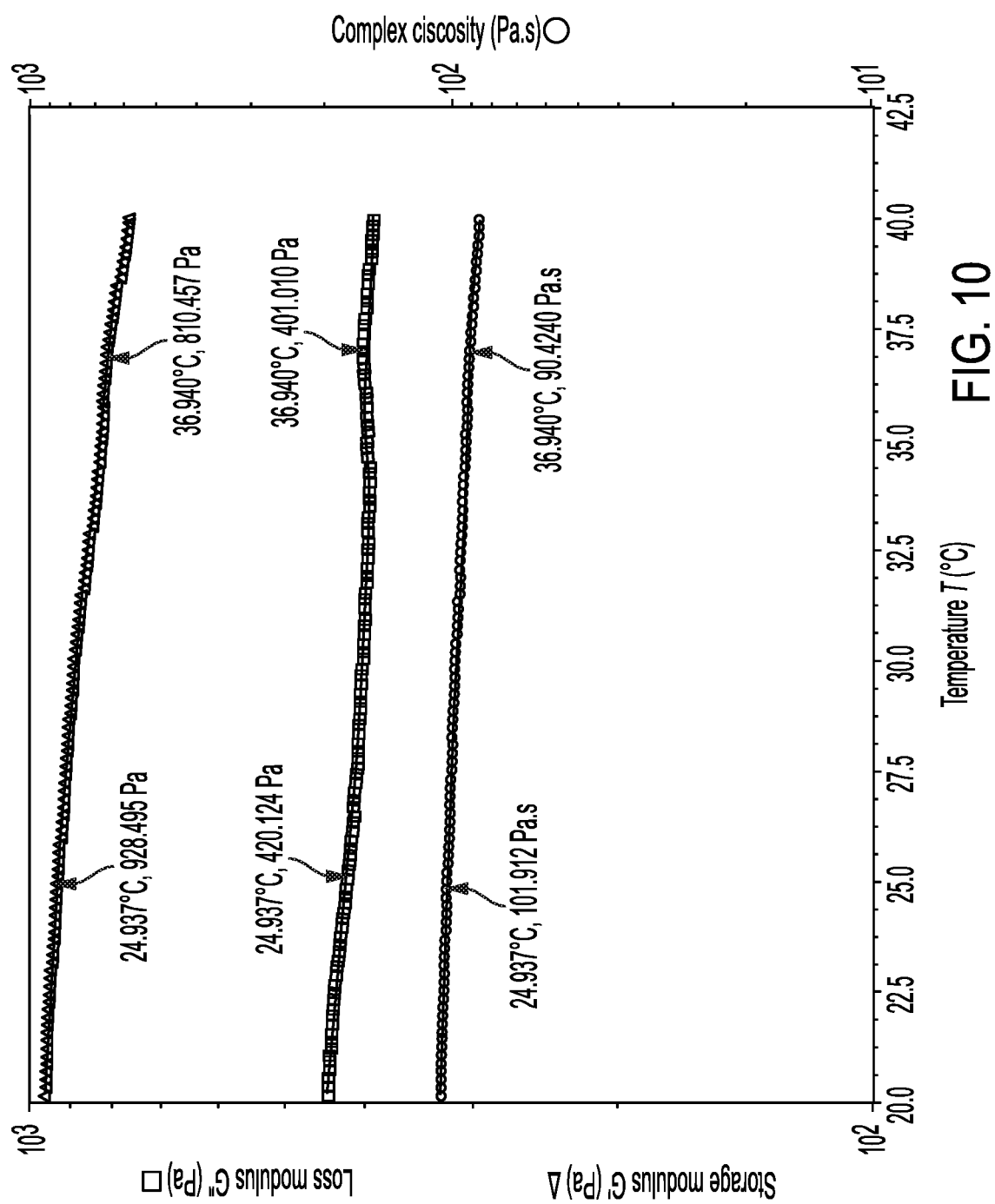
FIG. 10 is an oscillatory temperature sweep of Formulation #9 from 20° C. to 40° C.

Utilizing a flow stress sweep protocol, zero rate viscosities of 95 kPa-s and 105 kPa-s were determined at 25° C. and 37° C., respectively, for formulation #9 (FIG. 7A-7D). An oscillatory frequency sweep showed a mostly parallel relationship between the storage modulus (G') and the loss modulus (G") with some convergence at high frequency (FIG. 8A-8B). Further, no widening or hysteresis was observed across the frequency domain and the difference between G' and G" at 25° C. and 37° C. was observed to be negligible. An oscillatory amplitude sweep showed only a small difference between the crossover points of G' and G" and strains at 25° C. and 37° C., thus indicating the transition from solid-like to liquid-like is similar across the defined temperature range (FIG. 9A-9B). An oscillatory temperature sweep revealed a slight negative slope for G', G", and complex viscosity (FIG. 10). Further, this provided another piece of evidence in support of the negligible differences in Formulation #9 at 25° C. and 37° C. Taken in aggregate, these rheological properties demonstrate ideal properties for a vulvovaginal cream designed to be stored at room temperature and applied to anatomy at body temperature. These ideal properties were also observed in Formulation #11.

Comparison of Mechanical Properties and Osmolarities: Formulation #9 vs. Predicate Creams for Vaginal Application A comparison of the mechanical properties and osmolarities for Formulation #9 and predicate creams (e.g., Monistat 7, Vagisil, and 2% Clotrimazole) for vaginal application was performed, and the results are depicted in Table 3 below.

TABLE 3

Comparison of Mechanical Properties and Osmolarities

| Formulation | Zero-Rate Viscosity | Frequency Sweep Comparison | Amplitude Sweep Comparison | Osmolarity (mOsm/kg) |
| --- | --- | --- | --- | --- |
| Monistat 7 | 45 kPa-s @ 25 C. 95 kPa-s @ 37 C. | Some widening | 25 C. Crossover @ ~1800 Pa 25 C. Strain @ ~0.5% 37 C. Crossover @ ~1.9 Pa 37 C. Strain @ 1.3% | ND |
| Vagisil | 329 kPa-s @ 25 C. 142 kPa-s @ 37 C. | Some widening | 25 C. Crossover @ 386.8 25 C. Strain @ 29.2% 37 C. Crossover @ 326.2 Pa 37 C. Strain @ 30.4% | 1374 |
| Clotrimazole | 590 kPa-s @ 25 C. 281 kPa-s @ 37 C. | Some widening | 25 C. Crossover @ 2552.4 Pa 25 C. Strain @ 29% 37 C. Crossover @ 1703.3 Pa 37 C. Strain @ 5.4% | 125 |
| #9 | 95 kPa-s @ 25 C. 105 kPa-s @ 37 C. | No widening | 25 C. Crossover @ 323.6 Pa 25 C. Strain @ 10.4% 37 C. Crossover @ 435.6 Pa 37 C. Strain @ 11.3% | 300 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the claims.

Additional Exemplary Embodiments Include

In an embodiment, provided herein is a dermatological composition comprising a stable water-in-silicone emulsion having a continuous silicone phase and an aqueous phase, wherein the emulsion comprises a sterol at a concentration from about 0.1% to about 4% by weight, of the total weight of the composition. In embodiments, the sterol comprises cholesterol, or cholesterol derivatives.

In an embodiment, provided herein are methods for preventing or treating a dermatological condition in a subject, the method comprising administering to the subject a composition comprising a stable water-in-silicone emulsion, wherein the emulsion has a sterol at a concentration from about 0.1% to about 4% by weight of the total weight of the composition.

In an embodiment, provided herein is a rectal composition comprising a stable water-in-silicone emulsion having a continuous silicone phase and an aqueous phase, wherein the emulsion comprises a sterol at a concentration from about 0.1% to about 4% by weight, of the total weight of the composition. In embodiments, the sterol comprises cholesterol, or cholesterol derivatives.

In an embodiment, provided herein are methods for treating a rectal condition in a subject, the method comprising administering to the subject a composition comprising a stable water-in-silicone emulsion, wherein the emulsion has a sterol at a concentration from about 0.1% to about 4% by weight of the total weight of the composition.

In an embodiment, provided herein is a sunscreen composition comprising a stable water-in-silicone emulsion having a continuous silicone phase and an aqueous phase, wherein the emulsion comprises a sterol at a concentration from about 0.1% to about 4% by weight, of the total weight of the composition. In embodiments, the sterol comprises cholesterol, or cholesterol derivatives.

In an embodiment, provided herein are methods for preventing UV-radiation damage in a subject, the method comprising administering to the subject a composition comprising a stable water-in-silicone emulsion, wherein the emulsion has a sterol at a concentration from about 0.1% to about 4% by weight of the total weight of the composition.

In an embodiment, provided herein is a transdermal drug delivery composition comprising a stable water-in-silicone emulsion having a continuous silicone phase and an aqueous phase, wherein the emulsion comprises a sterol at a concentration from about 0.1% to about 4% by weight, of the total weight of the composition. In embodiments, the sterol comprises cholesterol, or cholesterol derivatives.

In an embodiment, provided herein are methods for treating pain, diabetes, neurological disorders or diseases, hormone deficiency, or nausea in a subject, the method comprising administering to the subject a composition comprising a stable water-in-silicone emulsion, wherein the emulsion has a sterol at a concentration from about 0.1% to about 4% by weight of the total weight of the composition.

In an embodiment, provided herein is an ophthalmic composition comprising a stable water-in-silicone emulsion having a continuous silicone phase and an aqueous phase, wherein the emulsion comprises a sterol at a concentration from about 0.1% to about 4% by weight, of the total weight of the composition. In embodiments, the sterol comprises cholesterol, or cholesterol derivatives.

In an embodiment, provided herein are methods for preventing or treating an ophthalmic condition in a subject, the method comprising administering to the subject a composition comprising a stable water-in-silicone emulsion, wherein the emulsion has a sterol at a concentration from about 0.1% to about 4% by weight of the total weight of the composition.

What is claimed:

1. A method for treating a vaginal condition in a subject, comprising:
    applying to a tissue surface a composition comprising a stable water-in-silicone emulsion having a continuous silicone phase and an aqueous phase,
    wherein the emulsion comprises a non-silicone emulsifier comprising cholesterol or a cholesterol derivative at a concentration from about 0.1% to about 4% by weight of the total weight of the composition and a sorbitan ester,
    wherein the composition does not utilize a silicone-based emulsifier,
    wherein the pH of the composition is from about 3 to about 5,
    wherein the composition has an osmolarity of about 200 to about 500 mOsm/kg,
    wherein the composition comprises glycogen, and
    wherein the composition is used in an amount effective to treat said vaginal condition in the subject, wherein said vaginal condition comprises vulvar and vaginal atrophy (VVA).

2. The method of claim 1, wherein the tissue surface comprises an epithelial surface or a mucosal surface.

3. The method of claim 1, wherein the vaginal condition further comprises bacterial vaginosis, vaginal dryness, vaginal itch, vaginal irritation, dyspareunia, bacterial infection, yeast infection, urinary tract infection, menopause, perimenopause, post-menopause, a sexually transmitted infection, sexually transmitted disease, or combinations thereof.

4. The method of claim 1, wherein the composition is administered to the tissue surface via topical administration, vaginal administration, or mucosal administration.

5. The method of claim 1, wherein the composition is formulated as a personal lubricant, as a moisturizer, as an ointment, as a lotion, as a topical cream, as a skin protectant, or for drug delivery.

6. The method of claim 1, wherein the composition further comprises one or more active agents.

7. The method of claim 6, wherein the one or more active agents comprise an antifungal agent, an antibiotics, a spermicide, estrogen, an estrogen derivative, progesterone, a progesterone derivative, an estrogen precursor, a steroid, an anti-inflammatory agent, an antiviral agent, an antiretroviral agent, a non-nucleoside reverse transcriptase inhibitor, a protease inhibitor, fusion inhibitors, an integrase inhibitor, or combinations thereof.

8. The method of claim 7, wherein the estrogen comprises estradiol.

9. The method of claim 1, wherein the emulsion further comprises a co-emulsifier.

10. A method for treating a vaginal condition in a subject, comprising:
    applying to a tissue surface a composition comprising a stable water-in-silicone emulsion having a continuous silicone phase comprising about 55% to about 75% by weight of the composition and an aqueous phase,
    wherein the emulsion comprises a non-silicone emulsifier comprising cholesterol or a cholesterol derivative at a concentration from about 0.1% to about 4% by weight of the total weight of the composition and a sorbitan ester,
    wherein the composition does not utilize a silicone-based emulsifier,
    wherein the pH of the composition is from about 3 to about 5,
    wherein the composition comprises glycogen,
    wherein the composition has an osmolarity of about 200 to about 500 mOsm/kg, and
    wherein the composition is used in an amount effective to treat said vaginal condition, wherein said vaginal condition comprises vulvar and vaginal atrophy (VVA).

* * * * *